US010181186B2

(12) United States Patent
Kriheli et al.

(10) Patent No.: US 10,181,186 B2
(45) Date of Patent: Jan. 15, 2019

(54) ROBOTIC SYSTEM FOR COMPOUNDING MEDICATION

(71) Applicant: EQUASHIELD MEDICAL LTD., Tefen Industrial Park (IL)

(72) Inventors: Marino Kriheli, Tel Aviv (IL); Eric Shem-Tov, Ramat Hasharon (IL); Gonen Daskal, Kfar Hanasi (IL)

(73) Assignee: EQUASHIELD MEDICAL LTD., Tefen Industrial Park (IL)

( * ) Notice: Subject to any disclaimer, the term of this patent is extended or adjusted under 35 U.S.C. 154(b) by 362 days.

(21) Appl. No.: 14/913,442

(22) PCT Filed: Aug. 24, 2014

(86) PCT No.: PCT/IL2014/050753
§ 371 (c)(1),
(2) Date: Feb. 22, 2016

(87) PCT Pub. No.: WO2015/029018
PCT Pub. Date: Mar. 5, 2015

(65) Prior Publication Data
US 2016/0200462 A1 Jul. 14, 2016

(30) Foreign Application Priority Data

Aug. 26, 2013 (IL) .......................................... 228122

(51) Int. Cl.
*G06T 7/00* (2017.01)
*G06F 17/30* (2006.01)
(Continued)

(52) U.S. Cl.
CPC ............ *G06T 7/0012* (2013.01); *B65B 3/003* (2013.01); *B65B 55/02* (2013.01);
(Continued)

(58) Field of Classification Search
CPC .......... B65B 3/003; B65B 3/04; A61J 1/2096; A61J 1/20; A61J 1/2055; A61J 7/0053;
(Continued)

(56) References Cited

U.S. PATENT DOCUMENTS 3,024,701 A   3/1962 Marks
8,196,614 B2  6/2012 Kriheli
(Continued)

FOREIGN PATENT DOCUMENTS

JP   2004-208842   7/2004
JP   2005-334056   12/2005
(Continued)

OTHER PUBLICATIONS

Department of Health and Human Services; Niosh Alert—Preventing Occupational Exposures to Anitneoplastic and Other Hazardous Drugs in Health Care Settings; 2004—58 pages.
(Continued)

*Primary Examiner* — Kenny A Cese
(74) *Attorney, Agent, or Firm* — Roach Brown McCarthy & Gruber, P.C.; Kevin D. McCarthy

(57) ABSTRACT

The invention is a system designed to assist a hospital pharmacy in the compounding of medications comprising hazardous drugs. The system comprising: a safety cabinet, at least two robotic arm assemblies configured to simultaneously move vials and syringes within the safety cabinet, a plurality of cameras each installed at a specific location in the safety cabinet or on the robotic arm assemblies, and a processor. Each of the cameras is dedicated to provide real time digital images of the stage of the preparation process carried out at its location. Dedicated software and algorithms in the system processor allow almost all steps in the compounding process to be carried out automatically by the robotic arm assemblies without intervention by the operator (Continued)

or a supervisor and the cameras and imaging process algorithms are adapted to provide real-time feedback control of all stages of the compounding process.

14 Claims, 16 Drawing Sheets

(51) Int. Cl.

| | | |
|---|---|---|
| *G06K 9/00* | (2006.01) | |
| *G06F 19/00* | (2018.01) | |
| *B65B 3/00* | (2006.01) | |
| *G07F 17/00* | (2006.01) | |
| *B65B 55/02* | (2006.01) | |
| *G06K 9/18* | (2006.01) | |
| *G06Q 10/06* | (2012.01) | |
| *G06Q 50/22* | (2018.01) | |
| *G08B 21/18* | (2006.01) | |
| *H04N 7/18* | (2006.01) | |
| *G06T 7/62* | (2017.01) | |
| *G16H 20/10* | (2018.01) | |

(52) U.S. Cl.
CPC .... *G06F 17/3056* (2013.01); *G06F 17/30247* (2013.01); *G06F 19/00* (2013.01); *G06F 19/3456* (2013.01); *G06K 9/00771* (2013.01); *G06K 9/00973* (2013.01); *G06K 9/18* (2013.01); *G06Q 10/06316* (2013.01); *G06Q 50/22* (2013.01); *G06T 7/62* (2017.01); *G07F 17/0092* (2013.01); *G08B 21/18* (2013.01); *G16H 20/10* (2018.01); *H04N 7/18* (2013.01); *B65B 55/027* (2013.01); *G06T 2207/30232* (2013.01)

(58) Field of Classification Search
CPC ...... A61M 5/1782; G06T 7/0012; G06T 7/62; G07F 17/0092; G07F 11/165; G07F 11/62; G06F 19/3462; G06F 19/3468; G06F 19/3456; G06F 19/326; G06F 17/30247; G06F 17/3056; G06F 19/00; G21F 5/018; Y10T 436/2575; B01F 13/1072; B01F 13/1055; G06K 9/00771; G06K 9/00973; G06K 9/18; G06Q 10/06316; G06Q 50/22; G08B 21/18; G16H 20/10
See application file for complete search history.

(56) References Cited

U.S. PATENT DOCUMENTS

| | | | |
|---|---|---|---|
| 8,267,127 B2 | 9/2012 | Kriheli | |
| 8,297,320 B2 | 10/2012 | Giribona | |
| 8,777,906 B1 | 7/2014 | Gray | |
| 9,744,300 B2 | 8/2017 | Kamen | |
| 2006/0259195 A1* | 11/2006 | Eliuk | A61J 1/20 700/245 |
| 2008/0169044 A1* | 7/2008 | Osborne | A61J 1/2096 141/1 |
| 2009/0198208 A1* | 8/2009 | Stavsky | A61J 1/2096 604/407 |
| 2010/0094653 A1 | 4/2010 | Tribble | |
| 2010/0119411 A1 | 5/2010 | Joshi | |
| 2011/0093279 A1 | 4/2011 | Levine | |
| 2012/0270310 A1* | 10/2012 | Spence | B01L 3/021 435/305.1 |
| 2012/0316897 A1 | 12/2012 | Hanina | |
| 2012/0318402 A1 | 12/2012 | Aguerre | |
| 2013/0142406 A1 | 6/2013 | Lang | |
| 2013/0204433 A1 | 8/2013 | Gupta | |
| 2014/0157731 A1* | 6/2014 | Perazzo | B65B 57/02 53/473 |

FOREIGN PATENT DOCUMENTS

| | | |
|---|---|---|
| JP | 2007-260390 | 10/2007 |
| JP | 2012-508076 | 4/2012 |
| JP | 2012-157604 | 8/2012 |
| JP | 5033267 | 9/2012 |
| WO | 2004/112685 | 10/2006 |
| WO | 2007/047138 A1 | 4/2007 |
| WO | 2011/033788 | 3/2011 |
| WO | 2014/122643 A1 | 8/2014 |
| WO | 2014/152828 A1 | 9/2014 |
| WO | 2014/181320 A1 | 11/2014 |

OTHER PUBLICATIONS

U.S. Pharmacopia, USPT 35- NF30, USP-NF General Chapter <797> Pharmaceutical Compounding—Sterile Preparations, 2011, 39 pages.
Kloth, Guide to the Prevention of Chemotherapy Medication Errors: Strategies to prevent chemotherapy errors: 2009, pp. 107-114.
Nebeket et al., High Rates of Adverse Drug Events in a Highly Computerized Hospital; Arch Intern Med/ vol. 165, May 23, 2005, pp. 1111 to 1116.
Walsh et al., Medication Errors Among Adults and Children with Cancer in the Outpatient Setting; J Clin Onco, 27: 891-896; 2008;.
MyHealthNewsDaily Staff. Nurses Exposed to Toxic Cancer Drugs, Study Finds, Aug. 24, 2011; 2 pages.
Couch et al.; Chemotherapy Drug Exposures at an Oncology Clinic—Florida, Health Hazard Evaluation Report, HETA 2009-0148-3158, 2012, 36 pages.
International Search Report from a counterpart foreign application—PCT/IL2014/050753—dated Dec. 24, 2014; 3 pages.
Written Opinion of the International Searching Authority from a counterpart foreign application—PCT/IL2014/050753—dated Dec. 24, 2014; 6 pages.
http://www.livescience.com/15721-nurses-exposed-toxic-cancer-drugs.html, Aug. 24, 2011 (4 pages).
Japanese office action with an English translation from a counterpart foreign application—2016-537596—dated Jul. 6, 2018 (7 pages).
Japanese office action from a non-counterpart application—2016-537597—dated Jun. 26, 2018 (8 pages).

* cited by examiner

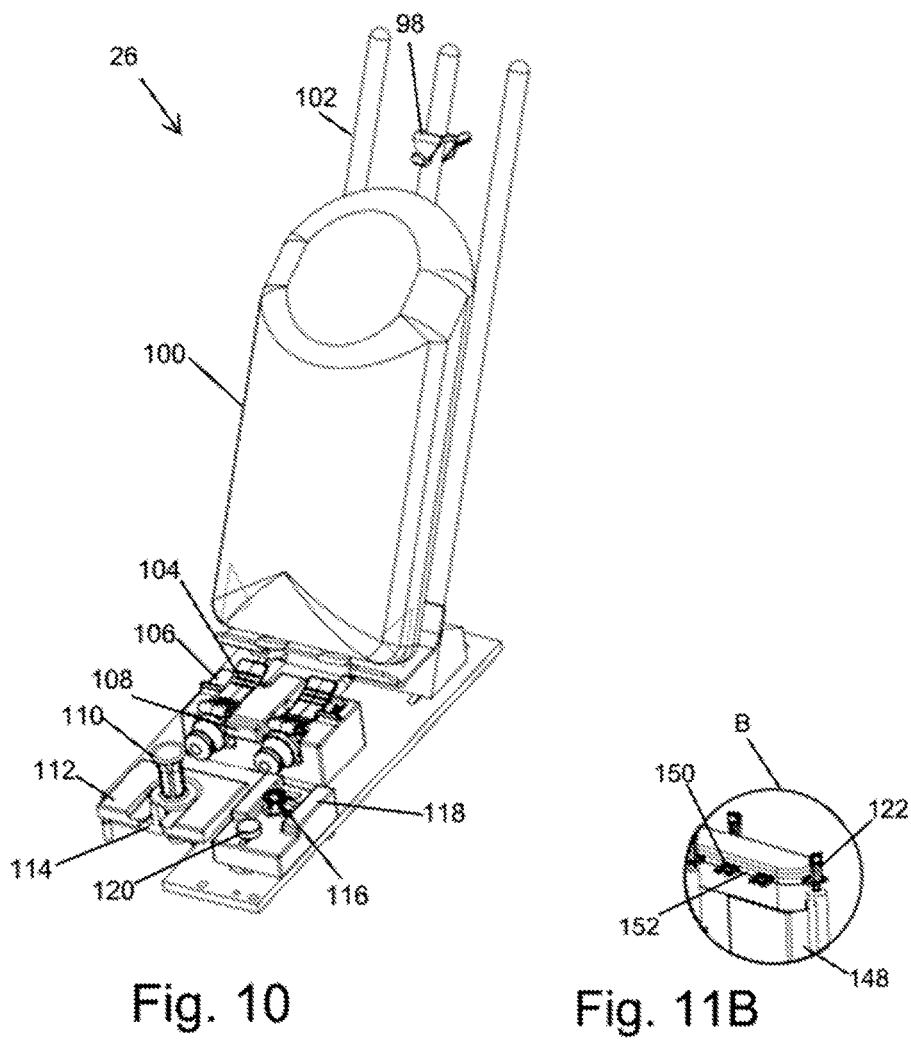
Fig. 10
Fig. 11B
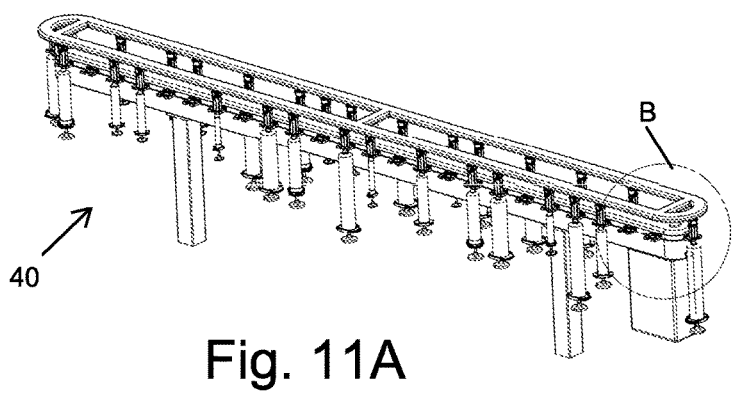
Fig. 11A

| Due | ID | Patient Name | Prescription / Diluent / Container |
|---|---|---|---|
| 14:21 | 000001 | | Paclitaxel [30mg] / 374ml NaCl 0.9% / Bag |
| 14:24 | 000002 | | Cisplatin [70mg] / NA / Syringe |
| 14:45 | 000003 | | Paclitaxel [50mg] / 250ml Dx5% / Bag |
| 14:54 | 000004 | | Cisplatin [30mg] / 300ml DX5% / CADD |
| 15:07 | 000005 | | Vincristin [3mg] / 150ml NaCl 0.9% / Bag |
| 15:09 | 000006 | | Vincristin [3mg] / 20ml NaCl 0.9% / syringe |

Ref_Point[492,480], Bubble_Ref_Point [492,754], Bubble Volume: 9.04 mL

Message Area

Fig. 18

ROBOTIC SYSTEM FOR COMPOUNDING MEDICATION

FIELD OF THE INVENTION

The present invention relates to the field of preparing drugs and medications for IV administration to patients. More particularly, the present invention relates to the field of automated systems for preparing drugs and medications for administration to patient.

BACKGROUND OF THE INVENTION

Publications and other reference materials referred to herein are numerically referenced in the following text and respectively grouped in the appended Bibliography which immediately precedes the claims.

In the common practice of chemotherapy prescription therapy the physician (oncologist) prescribes the type of medication the patient needs to take and the dosage per weight or body surface. When the medication is delivered intravenously, as in the majority of the cases, the patient is invited to come to a medical institute, usually a hospital, to receive the medication.

On the day of arrival, the patient's body indexes, e.g. weight and blood count, are measured. When ready, the prescription is sent to the hospital's pharmacy, together with the prescribed drug. With this information, together with the drug's instructions for use, the pharmacist will adjust the dosage in the prescription so that it matches the exact conditions of the patient on that particular day.

The prescription preparation process will usually involve using a syringe to draw a correct dose of concentrated drug from a drug vial and then injecting the drug into a final container, usually an IV bag, from which the drug will be delivered to the patient.

There are cases, in which the drug will come in a powder form in the vial and will need a primary dilution in the vial, before being used (this happens in about 20% to 50% of the cases).

There are 3 common intravenous delivery methods by which cytotoxic drugs are delivered to the patients: 1) Infusion (roughly 80% of all prescriptions)—in this method the drug is diluted into an IV-Bag (infusion bag) and the bag is delivered to the hospital ward. 2) IV-Push (about 20% of all prescriptions)—in this method a syringe is filled with the concentrated or diluted drug, and the drug is given by an intravenous shot directly from the syringe. 3) Infusion pumps comprising a cartridge into which the drug is diluted.

There are three factors that make chemo drugs, also known as antineoplastic drugs, unique among other drugs that are prepared in a hospital pharmacy:
1. Very low therapeutic index, which means a very narrow margin between an effective drug dosage and a harmful dosage.
2. Antineoplastic drugs are considered hazardous [1], [2] and therefore require extra and unique care when being handled, for the protection of the pharmacy and the hospital personnel.
3. The prescription dosage is customized to the conditions of the patient, on the day of delivery because: 1) the drug's low therapeutic index, which means that the dosage needs to be adjusted very carefully to the patients indexes on the day of delivery; 2) the shelf life of antineoplastic drugs, after being diluted, might be very short (sometimes as short as 30 minutes) meaning that prescriptions cannot be prepared in advanced; and 3) the cost of the drugs is very high, and the health institutions wish to avoid incidences in which a prescription was prepared for a patient that did not arrive at the hospital.

These three factors make the preparation of antineoplastic drugs a delicate and resource consuming process in hospital pharmacies.

The preparation of an antineoplastic drug prescription is carried out in very unique and highly supervised conditions:
1. There will usually be at list 2 professionals in charge of handling the preparation of the prescription; one that is in charge of data handling who in almost all cases is a certified pharmacist and a second who does the actual prescription compounding and might be a pharmacist or certified pharmacy technician. The first person (the pharmacist) will usually act as the process supervisor.
2. In order to protect the person who does the compounding, on one hand, and the sterility of the drug, on the other hand, strict environment conditions are required in the preparation room [2].
3. In recent years, observations have shown that, in spite of the strict preparation conditions, the hospital personnel that handle the hazardous drugs get exposed to them, through different (and sometimes surprising) exposure routes, the use of Closed System Transfer Devices (CSTD) such as those developed and manufactured by Equashield®, is becoming common and expected to become compulsory for the preparation of these types of drugs.

On one hand, the preparation of a chemotherapy prescription is very technical; pulling the correct dose from a vial, and transferring it to an IV bag (or any other container). On the other hand, three major difficulties are associated with the process:
1. Error control [3], [4], [5]:
    a. As stated above antineoplastic drugs have a very low therapeutic index, and any deviation from the correct dosage might either be non-effective, or highly dangerous.
    b. Administering the wrong drug to a patient might put him in great danger.
    c. When the patient is already waiting at the hospital, pressure of time under which the prescriptions are being prepared may make the pharmacy personnel prone to making mistakes.
2. Personnel Protection: Even after all the protection measures are taken still leakage and drips often occur—either because of human errors or equipment malfunction. These leakages put the hospital personnel and the pharmacy personnel under the risk of exposure to the drugs.
3. Preparation Capacity: As can be understood from the stated above, the exact prescriptions remain unknown to the hospital pharmacy up until the physiological indexes of the patient are measured. However, as soon as these indexes are taken, there is pressure of time to prepare the prescription as soon as possible, since the patient is now waiting for his medication and occupying a bed in the oncology ward. Since most patients come during certain hours during the day, this pressure increases. The pressure, together with the need for extra safety measurements, increase the risk for human errors, which in turn might lead to prescription preparation errors as well as to drug exposure because of careless work.

The combination of very technical and repeatable procedures, on one hand, and the need for high precision and caution, on the other hand, calls for the automatization of the process.

It is therefore a purpose of the present invention to provide an automated drug compounding system for the handling and preparation of hazardous and sterile drug prescriptions and specifically chemotherapy drugs.

It is another purpose of the present invention to provide an automated drug compounding system designed to be installed in the hospital pharmacy and be integrated with the data system handling the prescriptions at the hospital.

Further purposes and advantages of this invention will appear as the description proceeds.

SUMMARY OF THE INVENTION

The invention is a system designed to assist a hospital pharmacy in the compounding of medications comprising hazardous drugs. The system comprising:
  a. a safety cabinet;
  b. at least two robotic arm assemblies;
  c. a plurality of operational stations adapted to perform specific tasks related to the compounding process;
  d. a plurality of cameras each installed at a specific location in the safety cabinet or on the robotic arm assemblies, each camera dedicated to provide real time digital images of the stage of the preparation process carried out at that location;
  e. a system processor comprising: image processing algorithms to analyze the images received from the cameras; custom made algorithms to plan the timing and motions of the robotic arm assemblies and other devices inside the safety cabinet; custom made algorithms to execute the numerous comparisons and checks that are carried out to minimize errors in preparing the medications; and custom made software that manages the whole process and manages the data flow and the system database; and
  f. communication channels between the components of the system.

In the system of the invention:
  i. the robotic arm assemblies are adapted to simultaneously move vials and syringes within the safety cabinet;
  ii. the robotic arm assemblies are adapted to allow almost all steps in the compounding process to be carried out automatically under guidance of the software and algorithms in the system processor without intervention by the operator or a supervisor; and
  iii. the cameras and imaging process algorithms are adapted to provide real-time feedback control of all stages of the compounding process.

In embodiments of the system of the invention the safety cabinet comprises:
  a. a work area above a working surface, the work area divided by a partition into a forward section and a rear section; the work area comprising:
    i. at least one IV bag base module located in front of the partition;
    ii. at least one reconstitution module located behind the partition, each reconstitution module adapted to allow at least one vial to be connected to it and to inject a predetermined volume of liquid into the vial;
    iii. at least one vial shaker module located behind the partition, each vial shaker module adapted to allow one or more vials containing reconstituted drugs to be connected to it and shaken for a predetermined period of time and predetermined shaking method;
    iv. at least one vial flipper module located behind the partition, each vial flipper module adapted to allow at least one vial to be connected to it and to invert the vials;
    v. a vial insertion area located behind the partition;
    vi. a vial internal storage area located behind the partition; and
    vii. one vial robotic arm assembly comprising a vial gripper adapted to allow the vial robotic arm assembly to pick up and to rotate a vial, the vial robotic arm assembly adapted to allow it move a vial to any location behind the partition above the work surface and to release the vial at a new location or to connect the vial to and disconnect the vial from the reconstitution module, vial shaker module, and vial flipper module;
  b. a closed area below the working surface comprising;
    i. a syringe magazine comprising a plurality of syringe mounts attached to a conveyor belt driven by a motor, the syringe mounts adapted to allow a syringe to be hung on them by an operator; and
    ii. at least one syringe pump robotic arm assembly each syringe pump robotic arm assembly comprising a syringe gripper assembly and a syringe pump, adapted to pick up a syringe from the syringe magazine and to attach the syringe to a syringe pump, which is adapted to draw liquid into and to eject liquid from a barrel of the syringe; each syringe pump robotic arm assembly adapted to move a syringe to locations inside the closed area and to connect the syringe to and disconnect the syringe from vials, IV bags, and infusion pump cartridges; and to discard used syringes.
  c. an operator's display screen.

Embodiments of the system of the invention additionally comprise at least one of: a supervisor's station, a label printer, a backup memory device, and a programmable logic controller adapted to receive instructions from the system processor and to activate the robotic arm assemblies and other operational stations inside the safety cabinet.

In embodiments of the system of the invention, after a syringe pump has pulled a dose of drug from a vial, at least one image of the syringe is taken to check that there is no air bubble in the syringe barrel and to verify the position of the syringe piston in order to check that the correct volume of drug was pulled. In these embodiments, after it has been verified that the syringe pump has pulled the correct volume of drug and that there is no air bubble in the syringe barrel, the syringe pump robotic arm assembly can move the filled syringe to an IV bag base module and connect it to a final prescription container that is locked in the IV bag base and from which the drug is to be administered to the patient. If the final prescription container is the syringe, it is connected to a syringe plug or other syringe holder and disconnected from the syringe robotic arm assembly. If the final prescription container is an IV bag or an infusion pump cartridge the syringe pump is activated to push the contents of the syringe into the final prescription container and an image of the syringe is taken and analyzed to verify that the syringe is empty before disconnecting it from the final prescription container.

In embodiments of the system of the invention, a system operator can manually load vials into the vial insertion area in a random fashion. In these embodiments, after the vials have been randomly placed in the vial insertion area by the operator, a picture of the vial is taken and the position of each vial is determined by an image processing algorithm, to allow sending the vial robotic arm to pick the vials. In these embodiments, after the vials have been randomly placed in the vial insertion area by the operator, each vial is picked up by the vial robotic arm assembly and weighed and imaged and identified by the information on its label by the image processing algorithms and moved to a specific location in the vial internal storage area by the vial internal storage area.

In embodiments of the system of the invention, when a vial that has been previously placed in the vial internal storage area is required to fill a prescription, the software in the system processor sends instructions comprising the specific location at which the vial was inserted into the vial internal storage area to the vial robotic arm assembly.

In embodiments of the system of the invention, comprising one vial robotic arm assembly and two syringe pump robotic arm assemblies, the components of the system and the interactions between them are adapted to allow two prescriptions to be compounded in parallel.

Embodiments of the system of the invention comprise components adapted to supply ozone for sterilization of the entire interior of the safety cabinet or for sterilization of specific locations within the safety cabinet In embodiments of the system of the invention the components of the system and the interactions between them are adapted to allow separately performing each of the following pairs of operations:
 a. reconstituting the drug in a vial while simultaneously identifying other vials;
 b. identifying syringes simultaneously while identifying vials;
 c. reconstituting the drug in a vial while simultaneously identifying syringes;
 d. identifying vials while simultaneously either drawing a drug from a vial into a syringe or injecting a drug from a vial into a final prescription container;
 e. identifying syringes while simultaneously either drawing a drug from a vial into a syringe or injecting a drug from a vial into a final prescription container; and
 f. reconstituting the drug in a vial while simultaneously either drawing a drug from a vial into a syringe or injecting a drug from a vial into a final prescription container.

All the above and other characteristics and advantages of the invention will be further understood through the following illustrative and non-limitative description of embodiments thereof, with reference to the appended drawings.

BRIEF DESCRIPTION OF THE DRAWINGS

FIG. 10 schematically shows an IV bag base;
FIG. 11A schematically shows the syringe magazine;
FIG. 11B is an enlarged view of area "B" in FIG. 11A;
FIG. 18 shows an embodiment of a supervisor screen.

DETAILED DESCRIPTION OF EMBODIMENTS OF THE INVENTION

Figure 1:
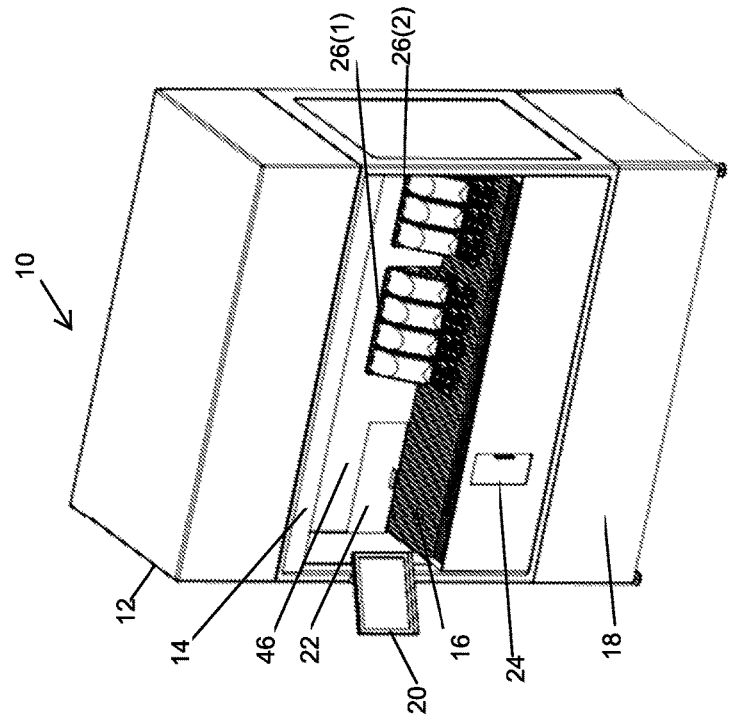
FIG. 1 is a schematic general view of the safety cabinet of the invention.

The invention is a system designed to assist a hospital pharmacy in the preparation of hazardous drugs and chemotherapy drugs in particular. The system is meant to be placed in the preparation room at the hospital pharmacy.

The three main goals of the system are: 1) Reduce human errors in the preparation of the prescriptions 2) Protect the employees who handle the hazardous drugs. 3) Improve the prescription preparation output rate at the pharmacy. The system of the invention is an automated system, controlled by software.

In order to achieve these goals the system of the invention comprises inter alia the following features:
 1. Synchronous operation: as further described below, unlike existing systems that process the prescriptions in series, the compounding tasks are handled by the system simultaneously, thereby allowing two prescriptions to be compounded in parallel.
 2. Image processing control: All the critical processes executed in the system are controlled by a plurality of cameras installed in the cabinet of the system combined with custom-made image processing algorithms. Each of the cameras is installed at a specific location in the safety cabinet and is dedicated to provide real time digital images of the stage of the preparation process carried out at that location. Image processing based control allows the system of the invention to operate smoothly and rapidly, with no need to pause compounding processes in order to weigh components, or for calibration. The image processing functions allow a cost effective and real-time feedback control over delicate and critical processes during the prescription preparation process. An additional advantage of the visual control is a complete image based documentation of the compounding process. This documentation will be kept in the system's archive for future use, if needed.
 3. The use of Equashield® connectors: The system can be designed to work with standard open system vials, syringes, IV bags, and connectors; however, when preparing chemotherapy drug prescriptions, while using open systems, e.g. standard syringes and needles, spills and aerosol release always occur. When using a prior art compounding system, the process may be conducted in a closed cabin, and without the involvement of a human hand; but, when spills and aerosol release occur, the compounding components, i.e. the compounded drug containers and the drug vials (which might be re-used later on) become contaminated. This contamination is carried with the containers out of the system and outside the pharmacy, to less protected areas and less aware people who then become exposed to the drugs [6], [7]. To prevent this danger, the embodiment of the system described herein operates uniquely and solely with Equashield® Closed-System Transfer Devices. These devices are described elsewhere, for example in U.S. Pat. No. 8,196,614, U.S. Pat. No. 8,267,127, PCT/IL2014/050112, and PCT/IL2014/050319. These devices are characterized by their ease of connection and safety. The use of Equashield® connectors allows the system of the invention to provide a third layer of protection—the 1st layer is working in a closed cabinet and the 2nd layer is using a robotic system to handle the drugs—for the pharmacy personnel, as well as for the hospital personnel that deal with the compounded drug containers later on.

The system of the invention is designed to operate in a large safety cabinet, for example a double size Biological Safety Cabinet Class II B2. The system consists of three robotic arm assemblies—one for vial handling and the other two, which each comprises a syringe manipulator (syringe pump) at its end, for compounding—and additional operational stations, which all operate synchronously.

Four classes of personnel, each allowed by the system to carry out clearly defined operations, are engaged in operation of the system:

Administrator—There is one administrator for the system. The administrator inter alia defines new users to the system and has all permissions of a supervisor.

Supervisor—The duties of the supervisors are inter alia to control the prescription lists and the workflow within the system. Supervisors are generally pharmacists.

Operator—The duties of the operators are inter alia to load drug vials, syringes, and IV bags into the system according to the prescription lists entered by the supervisor and take the ready drug containers, into which the drug has been compounded out of the safety cabinet. Operators are generally pharmacist assistants.

Technician—Technicians perform routine and emergency maintenance on the system and its components.

The invention's process control heavily relies on image processing, and the supervision of core processes is done using image processing technology. Complete documentation of the drug preparation process is based on a visual archive of the preparation steps, in which every step in the preparation process is documented and indexed in various ways, e.g. by the patient's or pharmacist's or doctor's identity or by date, and initially stored in a memory unit. The saved data/documentation can comprise such information as: time stamps; prescriptions details; patient identification and information, e.g. sex, age, weight, height, disease being treated; preparation phase details, e.g. comments, confirmations, alerts; log messages, e.g. errors, warnings, trace, debug; identification and verification of supervisor's permission if required; details of the operator that prepared the prescription and the supervisor; a visual archive of images taken during the preparation phase; and information regarding the dispensing phase.

The system of the invention comprises an internal database that is updated manually, according to the hospital guidelines, by an administrator and/or automatically from the hospital's databases. In embodiments of the invention the system can be connected to external databases of other hospitals, health institutes (e.g. FDA=Food and Drug Administration and NIH=National Institute of Health) and manufacturers, via a communication network.

Typical of the wide variety of information that can be included in the system's database and used by the algorithms in the software of the invention is:

a) National Drug Code (NDC) numbers, barcodes, packaging dosage, physical properties, reconstitution, dilution dosages and dispensing instructions etc. of drugs. The information can be continuously updated, either automatically or manually, with information from sources such as the FDA, NIH and medicines companies.

b) Capacity, catalog numbers, National Drug Code (NDC) numbers, barcodes, or other identifying features of IV Bags. The information is continuously updated, either automatically or manually, with information from the FDA, NIH and producer companies.

c) Capacity, catalog numbers, dimensions or other identifying features of syringes and adaptors. The information is continuously updated, either automatically or manually, from sources such as catalogues of medical products manufactures and distributers.

d) Images and video streams, both raw and processed taken by the system camera/s.

In one embodiment of the system, the system automatically compares dosages and diluents on the prescription to data in the drug manuals, or other data inserted into the system's database and verifies that the prescribed doses comply with the recommended dose tolerances in order to avoid errors and resulting wrong dosages. In case of differences between the prescribed and recommended doses the system sends an alert via the interface to the producer, i.e. the pharmacist, pharmacist technician or other person using the system of the invention, and optionally to the prescribing doctor or other hospital personnel.

The workflow of the system is as follows:

1. Prescription In-Flow: The system receives a full report sent from the supervising pharmacist containing inter alia: patient name, order number, drug type and dosage, container type, diluent type, diluent volume, and time to be delivered. From this report it generates a component list, consisting of the types, sizes, and quantities of syringes, drug vials and final containers (IV-bags, infusion pump cartridges or IV-push syringes), which are required for the preparation of the prescriptions. The component list is presented to the operator (usually a pharmacy technician) on an interactive touch-screen, attached to the system cabinet. It is noted that the system can be operated in several modes either dealing with the preparation of one prescription at a time or several prescriptions simultaneously. In different operating modes the supervisor can decide to send a list containing several preparations or he can send them one by one. The operator can choose if he wants to feed the machine with the components in batches for several prescriptions at one time or feed components for one prescription at a time 2. Components Loading: The system operator, in turn, feeds the system with the required components: drug vials are put in a free manner in an insertion area, syringes are put on a convoy, and IV bags, or other drug containers are put in dedicated places together with the prescription sticker. It is noted that, unlike other systems, in which the vials and other components need to be fed into very specific mounts and sometimes need to be grouped according to the specific prescription being filled, in the system of the invention vials are put into the vial area randomly. Then a vial position camera takes an image of the vial insertion area and image processing algorithms determine the location of the vial. The location of the vial is transmitted to the vial robotic arm assembly, which travels to that location and picks up and weighs the vial. It is also important to note that components can be fed into the system, regardless of the requirements of the prescriptions being handled. The system stores spare components for future use. All the feeding processes can be handled simultaneously and in random order, i.e. syringes fed before vials or vice versa.

After components are fed into the cabinet, the system handles them as follows:

a) Vials are picked by the vial robotic arm assembly, the type and quantity of drug in the vial is identified using image processing on camera images of the vial label, and the vial is weighed to estimate the volume of drug that remained in it, in case the vial has been previously used. If the drug needs to be reconstituted it is taken to a reconstitution station and later to a vial shaker. Otherwise, the vial is taken to an internal storage area where it is kept for future use.

b) Syringes are identified according to their size and the position of their plunger is determined, using image processing.

c) IV bags are photographed together with the prescription stickers that have been attached to them.

3. Component Verification: following "reading" of a prescription label by the image processing algorithms, the system searches for that prescription, in its database. If it finds a match, the system then checks: 1) that enough vials and syringes have been fed into the system for that prescription. 2) That the IV bag or other container matches the prescription. If all is correct, the system locks the container to its base and a compounding process begins.

4. The Compounding Process: The syringe convoy brings a correct size syringe to a picking point. One of the compounding, i.e. syringe, robotic arm assemblies moves to the syringe convoy and picks the correct syringe size. Simultaneously, the vial handling robotic arm assembly collects the correct drug vials and connects them to a vial flipper, which, in turn flips the vials up-side down. A compounding, i.e. syringe, robotic arm assembly in turn, brings the syringe to the drug vial, connects it to the vial adaptor, and a syringe pump that is a part of the compounding robotic arm assembly pulls the correct dose. When the correct dose has been pulled, two images of the syringe are taken: the first to verify the position of the syringe piston to check that the correct volume of drug was pulled and the second to check that there is no air bubble in the syringe barrel. If all is OK the syringe is disconnected from the vial adaptor, and connected to a spike adaptor, or any other container adaptor, and the syringe pump is activated to inject the drug into the final container. When the process is finished, a 'Finish' sticker is printed and attached to the container by the operator. An image of the final container is now taken and if the image processing algorithms determine that the correct 'Finish' sticker has been attached to the container, the container lock opens-up and the operator is prompted to take the ready prescription out of the cabinet.

As stated above, due to its modular architecture and the independence between the different modules, all processes in the system can run simultaneously:

Component Feeding: Syringes can be fed to the system, while vials are being fed, while bags are being fed.

Component feeding, drug reconstitution and drug compounding are all independent of each other and can run simultaneously.

Since there are two compounding modules and two compounding robotic arm assemblies, 2 compounding processes can be handled in parallel.

While all processes take place, new prescriptions can be fed to the system.

The image processing functions integrated in the system allow, on one hand, a highly controlled process, and on the other hand, a fast, smooth and user-friendly operation. Some of the more innovative of these functions are:

1. Vial position recognition: As described above, the vials are inserted into the system, by placing them in a random manner in a dedicated area of the cabinet. After placing the vials, the system takes an image of them and analyses their position in order to be able to send the vial robotic arm assembly to collect them.

2. Vial label recognition: After being collected by the robotic arm assembly, the vial is turned in front of a camera and is identified by analyzing its label before the robotic arm assembly places it in an internal storage area or a reconstitution module. The vial is identified a second time, when picked from the system's internal storage area, just before compounding.

3. Syringe size determination: The size of the syringe, as it is loaded to the syringe system, is determined by image processing.

4. Dosage verification: Two image processing functions are at the heart of the system of the invention:

a. Volume recognition: When drawing a drug into a syringe, this function determines the volume to which the syringe was pulled by measuring the position of the syringe piston. The value of the volume determined by this function is compared with the output of the syringe plunger manipulator, to verify that the two values match. The syringe volume is checked twice: Once, before injecting the drug to the IV bag, to verify that the correct drug volume was pulled into the syringe and second, after injecting the drug into the IV bag, to verify that the syringe has been emptied.

b. Bubble recognition—Even if the plunger is pulled to fill the syringe with the correct volume, the syringe might still contain an air bubble. The bubble recognition imaging function, combined with very specific conditions for lighting the syringe barrel allows the system to determine whether the syringe barrel contains an air bubble and, if a bubble is present, to calculate the bubble's size.

5. Prescription sticker recognition: When an IV bag is fed into the system, the prescription, for which it is designated, is attached to it. By taking an image of the sticker and analyzing its content, the system matches the correct prescription to the bag, to allow the compounding process to begin.

6. Finish sticker recognition: At the end of a successful compounding process, the system prints a finish sticker, dedicated to the specific prescription. Only when the system recognizes that the sticker has been attached to the correct bag, do the bag locks open, allowing the bag to be collected.

7. Archiving: All key images during the process of compounding a prescription are stored in the system's archive, together with other data concerning the prescription.

Figure 17:
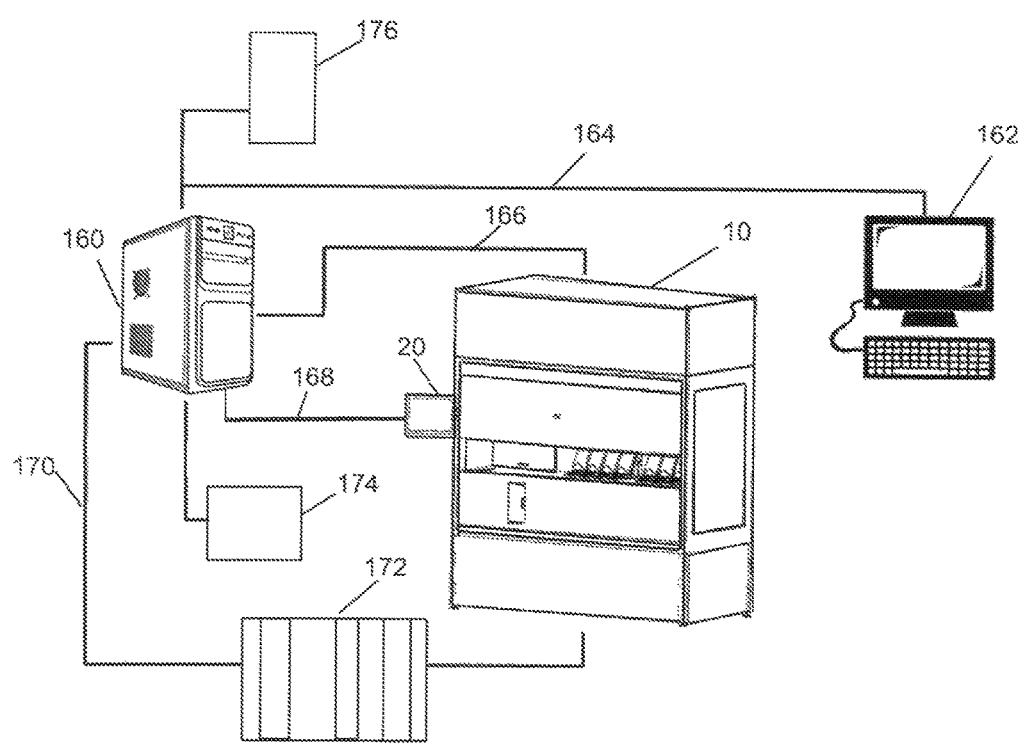
FIG. 17 schematically shows the main components of the system of the invention.

FIG. 17 schematically shows the main components of the system of the invention. The heart of the system is the safety cabinet 10 and system processor 160, which can be implemented with for example a personal computer (PC). The processor comprises inter alia custom-made image processing algorithms to analyze the images received from the cameras, custom made algorithms to plan the timing and motions of the robotic arm assemblies and other devices inside the safety cabinet in order to maintain efficient continuous preparation of the prescriptions, and custom made algorithms to execute the numerous comparisons and checks that are carried out to minimize errors in preparing the medications. Processor 160 also includes the software that manages the whole process and manages the data flow and the system database.

Images from cameras in the safety cabinet are sent to the system processor via camera communication channel 166. Instructions to control the motions of the robotic arm assemblies and other components inside the safety cabinet are sent from the system processor 160 via motion control communication channel 170 and Programmable Logic Controller (PLC) 172.

Data is fed to the system processor via data communication channel 164 from the supervisor's station 162, which comprises a display screen and input means and communicates also with external sources such as the hospital's data base and the internet.

FIG. 18 shows an embodiment of a screen shot on the supervisor's display screen. This screen shot comprises a list of prescriptions to be prepared and the time when the preparation must be completed to administer them to a patient. The supervisor can change the order in which the prescriptions are to be filled. In the lower left corner of the screen is a message area in which the supervisor receives messages from the system and in the lower right corner a window in which is displayed an image from one of the cameras in the safety cabinet that is selected by the supervisor. The menu allows the supervisor to select other screens, for example a screen that allows him to follow the progress of the preparation of a specific prescription, a screen that enables him to know what activity each of the components inside the safety cabinet, e.g. the robotic arms, is doing at any time, and screens that show what is being displayed on the operator's screen.

Figure 19:
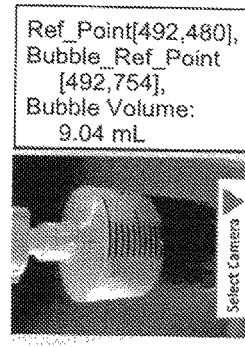
FIG. 19 shows an embodiment of an operator screen.

Information between the supervisor and the system processor's software are fed via communication channel 164. FIG. 19 shows a typical screen shot on the operator's display screen 20. This screen shot displays the list of prescriptions and due times sent by the supervisor, a listing of the required final containers and which of the posts on the IV bag base modules to which the operator should attach them, and a listing of the drug vials and syringes that the operator should take from the pharmacy's store and insert into the safety cabinet. The operator also has various options displayed on this and other screens that enable him to view the camera images monitor the progress of the preparations, change the order in which the prescriptions are filled, etc.

Also connected to system processor 160 are a label printer 174 and a backup memory device 176. All communication channels are implemented using standard wired or wireless technologies.

Figure 2:
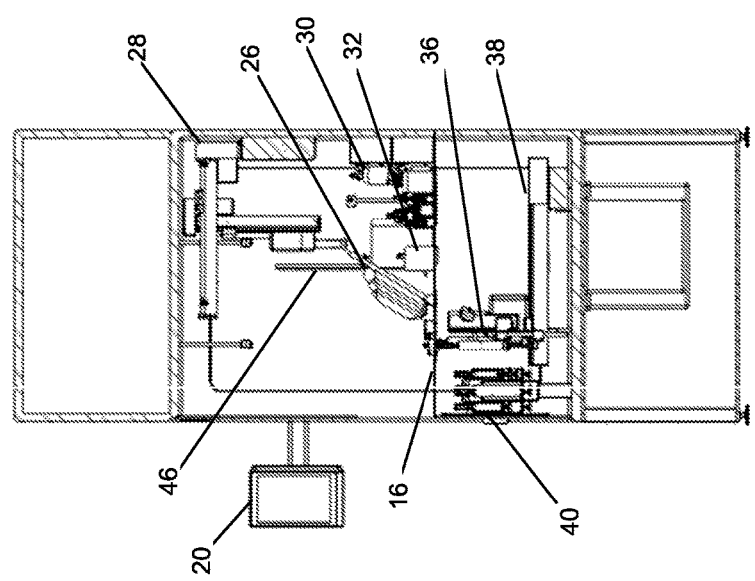
FIG. 2 is a cross-sectional view of the safety cabinet of the invention.

FIG. 1 is a general view and FIG. 2 is a cross-sectional view of the safety cabinet 10 of the invention. The top part of the cabinet is a HEPA filter housing 12, which contains the filter and exhaust fans.

Below housing 12 is a work area located above an at least partially perforated working surface 16. This area is divided by a partition 46 into a forward section that is open to the operator and a rear section that the operator can only access to manually insert vials through vial insertion door 22. On work surface 16 in front of partition 46 are two IV bag base modules 26(1) and 26(2) to which the operator can attach IV bags. Behind partition 46 is an area containing operational stations used to manipulate the vials. Seen in FIG. 2 are shakers 30, vial flip mechanisms 32, and vial robotic arm assembly 28.

Seen in FIG. 1 is operator screen 20, which allows communication between the operator and the system, and pull-down window 14, which can close off the front of the cabinet when the operator or a technician does not have to be working inside the cabinet.

Seen on FIG. 2 below working surface 16 is a closed area that contains syringes and the sub-systems, including syringe pumps 36 and one of the two syringe pump robotic arm assemblies 38 that are used to manipulate and move them. This area is normally closed to the operator who can only access it to manually insert syringes into the syringe magazine 40 through syringe insertion door 24.

At the bottom of safety cabinet 10 is a closed cabinet that houses the electrical components, electronics circuit boards, system processor, and waste disposal containers.

It is to be understood that all of the figures herein schematically show a specific embodiment of the safety cabinet in order to illustrate the invention. The figures are not drawn to scale and the numbers of specific items shown and described are not meant to be limiting. For example, in the cabinet described herein there are two IV base module sets 26(1) and 26(2)—each of which comprises four IV modules; however in other embodiments there can be more or less sets and/or more or less modules per set. It is noted that in the embodiment described herein there are two.

Figure 3:
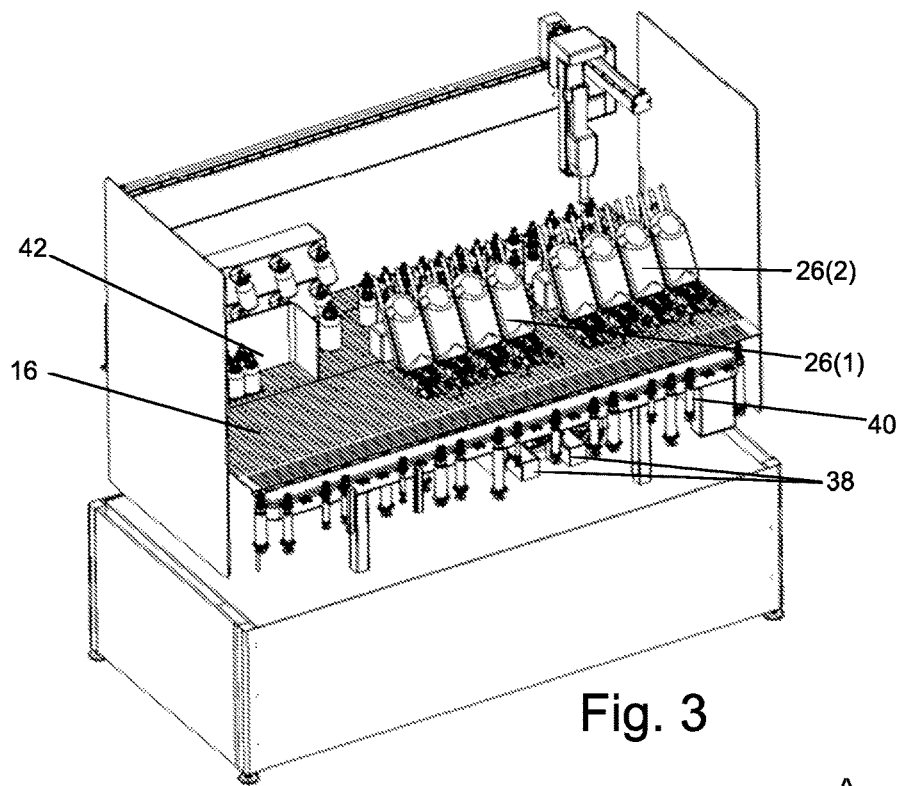
FIG. 3 is a schematic view of the safety cabinet with part of the external walls and interior partition removed to show how the internal space is arranged to receive the vials, syringes and IV bags.

FIG. 3 is a schematic view of the safety cabinet with part of the external walls and interior partition 46 removed to show how the internal space is arranged to receive the vials, syringes and IV bags that are "loaded" into it by the operator. In FIG. 3 are shown the vial insertion area 42, the IV bag base modules 26(1) and 26(2), the two syringe pump robotic arm assemblies 38, and the syringe magazine 40.

Figure 4B:
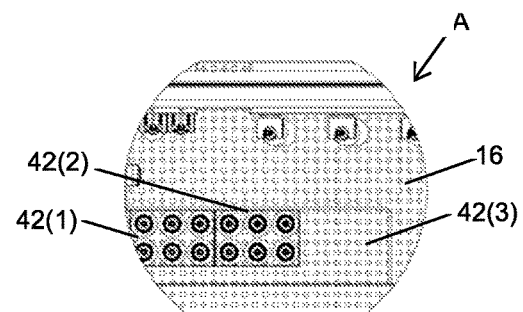
FIG. 4B is an enlarged view of area "A" in FIG. 4A.
Figure 4A:
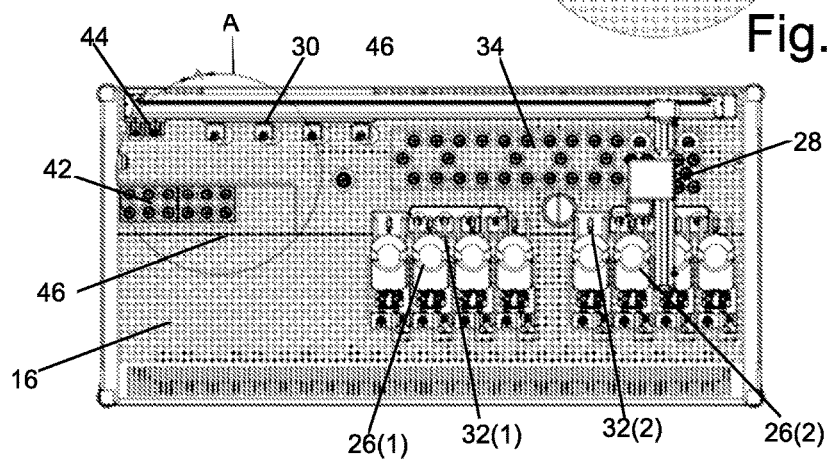
FIG. 4A is a schematic top view of the working surface.

FIG. 4A is a schematic top view of the working surface 16. In front of partition 46 are the two IV bag base module sets 26(1) and 26(2). Behind partition 46 is the vial insertion area 42, which as shown in FIG. 4B is divided into an area 42(1) for vials containing drugs that have to be reconstituted, a second area 42(2) for vials containing ready to use drugs and s third area 42(3), which is an extraction area where the vial robotic arm assembly places vials that should be taken out of the cabinet when ordered by the operator, after part of the contents have been withdrawn (and the remainder can be returned to the pharmacy storage for future use, or if a vial cannot be identified. After the vials are manually placed in areas 42(1) and 42(2) by the operator, each one is picked up by the vial robotic arm assembly and weighed and imaged and identified by the information on their labels by the image processing algorithms and then moved either directly to vial internal storage area 34 or to reconstitution module 44 by vial robotic arm assembly 28. The vials are moved from reconstitution module 44 to one of two shakers 30 and then to vial internal storage area 34 by vial robotic arm assembly 28. Finally vial robotic arm assembly 28 moves vials from the vial internal storage area 34 to one of the two vial flip mechanisms 32 arranged in two arrays 32(1) and 32 (2), each comprising four vial mounts.

Figure 5:
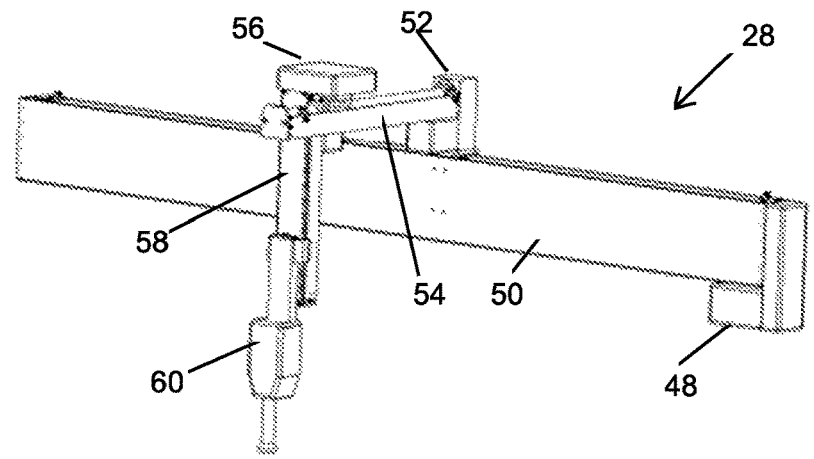
FIG. 5 schematically shows vial robotic arm assembly.

FIG. 5 schematically shows vial robotic arm assembly 28. Under direction of the software of the system vial robotic arm assembly 28 is configured to pick up vials, move them to any location on working surface 16 behind partition 46; to connect and disconnect them from reconstitution module 44, shakers 30, and flip mechanisms 32; and to release them at a new location on working surface 16 or in a discard bin. The degrees of motion required to carry out these tasks are provided by a mechanical arrangement, for example, an x-axis motor and gear box 48 that turn a screw, a chain, or a belt, to move y-axis motor and gear box 52 in the x-direction along x-axis beam 50. Y-axis motor and gear box 52 turns a screw to move z-axis motor and gear box 56 in the y-direction along y-axis beam 54. Z-axis motor and gear box 56 moves vial gripper assembly 60 up and down in the z-direction along z-axis beam 58. Motors 48, 52, and 56, as well as all other motors in the system, are reversible electrical motors.

Figure 6A:
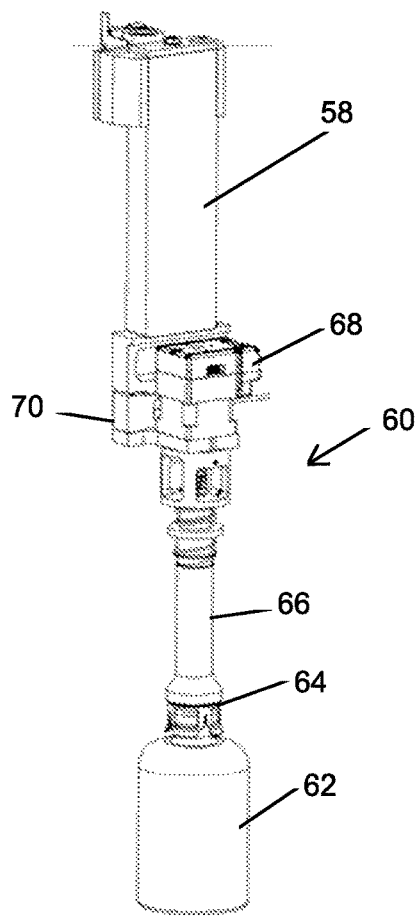
FIG. 6A schematically shows the vial gripper assembly.
Figures 6B, 6C:
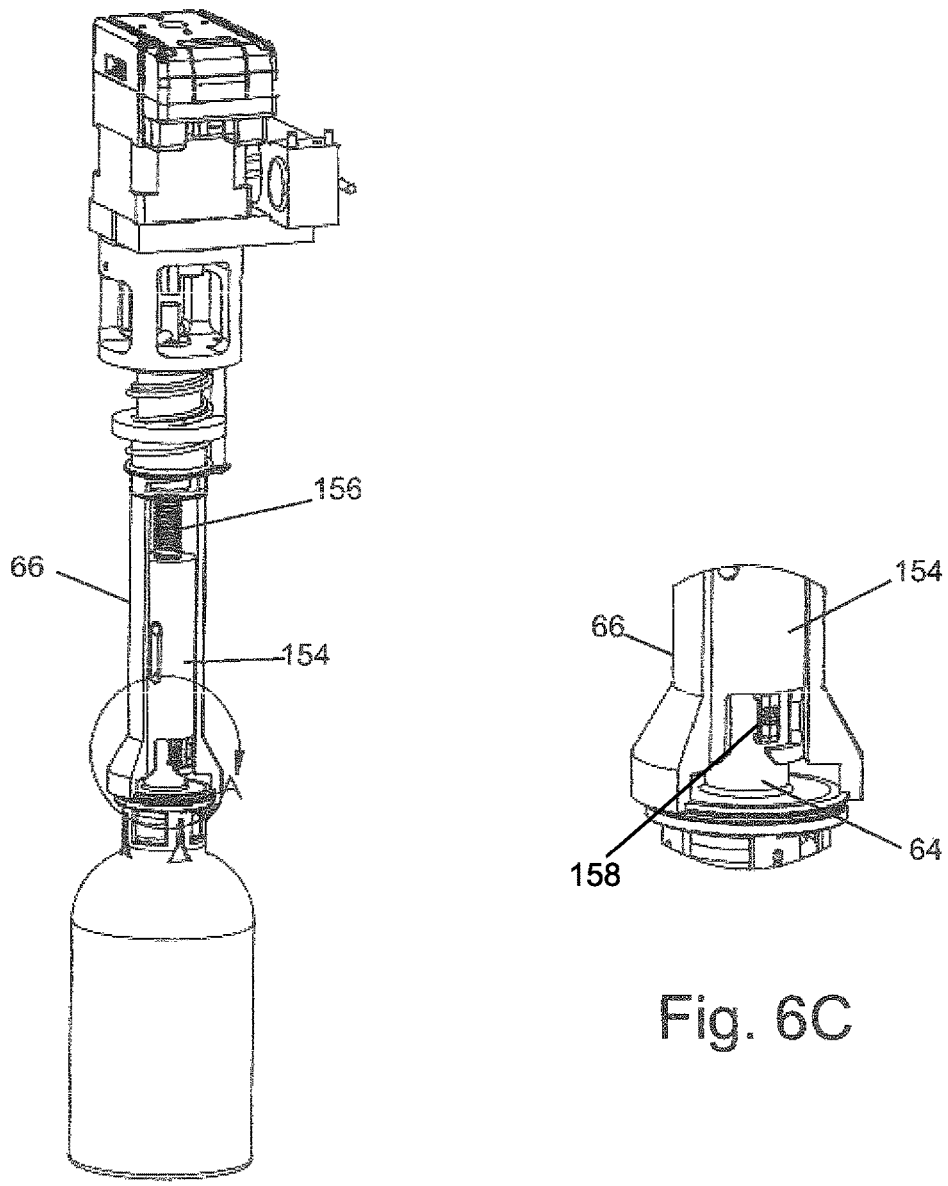
FIG. 6B schematically shows vial gripper assembly 60 with part of the wall of vial gripper removed to reveal some of the inner components.
FIG. 6C is an enlarged view of section "A" in FIG. 6B.

FIG. 6A schematically shows the vial gripper assembly 60. The main components of the vial gripper assembly are a motor 68, a load cell 70 to give an estimate of the amount of drug in the vial, and a vial gripper 66, which is adapted to connect to an Equashield© vial adapter 64. In order to pick up a vial, the control system activates motors 48 and 52, to position vial gripper directly above the vial adapter 64 that is attached to vial 62, then it activates motor 56 to press the vial gripper 66 on the vial adaptor 64. FIG. 6B schematically shows vial gripper assembly 60 with part of the wall of vial gripper removed to reveal some of the inner components. FIG. 6C is an enlarged view of section "A" in FIG. 6B. When the vial gripper 66 is pressed against vial adaptor 64, the vial gripper hook 154 is pressed between the vial gripper spring 156 and a protrusion 158 on the side of the neck of the vial adaptor 64. Gripper motor 68 is then activated to turn the vial gripper hook 154 until the slot of the hook is above protrusion 158. Then the vial gripper spring pushes the hook down and catches under protrusion 158. The z-axis motor 56 is then activated in the reverse direction to raise the vial gripper 66 and attached vial 62 allowing the robotic arm 28 to be activated to move the vial to a designated location. To disconnect the vial from the vial gripper after it has arrived at the designated location motor 56 moves the vial down until the vial rests on the surface and vial gripper 66 is pressed against the vial adapter. Then motor 68 turns the vial gripper hook 154 in the reverse direction until it releases its grip from the protrusion 158 on the neck of the vial adapter. When the vial has been engaged by vial gripper 66, vial gripper motor 68 can be activated to rotate the vial gripper hook 154 and attached vial 62 in front of a camera to allow the label on the vial to be imaged.

Figure 7:
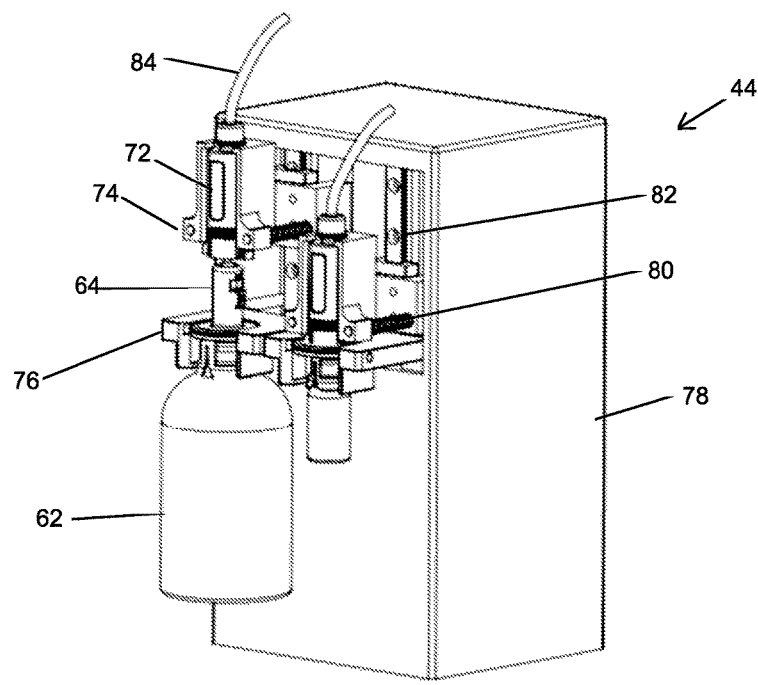
FIG. 7 schematically shows the reconstitution module.

FIG. 7 schematically shows the reconstitution module 44. The reconstitution module 44 comprises two reconstitution grippers 76 that are adapted to grip, for example, series 13 and 20 Equashield© vial adaptors 64, which have the same diameters. There are two positions in the module, to allow the injection of two types of fluids, e.g. saline solution and sterile water. An Equashield© Female Luer Lock connector, which may comprise two needles, to let fumes out of the vials 72 is attached to the reconstitution mount 74 before the compounding process begins and is used for several reconstitution sessions. The reconstitution mount 74 is pushed backwards by the vial gripper 66 on the vial robotic arm assembly 28 when the vial robotic arm assembly 28 inserts vial 62 into the reconstitution gripper 76. After vial gripper 66 releases its grip on the vial adapter 64, reconstitution mount 74 is returned to its original position by horizontal spring 80. Now reconstitution mount 74 is pushed downward on vertical rail 82 by an electrical motor+mechanism (located inside housing 78 and not seen in the figure) causing the Equashield© Female Luer Lock connector 72 to connect to the Equashield© vial adaptor 64. When connected, a pump (not shown in the sketch) injects the right dose of fluid into the vial through the hose 84.

Figure 8:
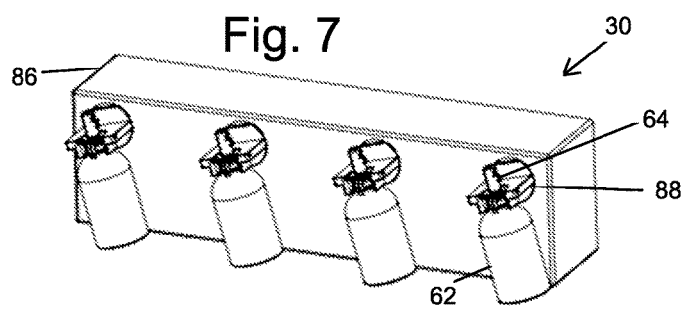
FIG. 8 schematically shows the vial shakers and the shaker housing.

FIG. 8 schematically shows one of shakers 30 and the shaker housing 86. Each Equashield© vial adapter 64 attached to vial 62 is shown after the vial robotic arm assembly 28 has inserted it into a shaker vial gripper 88 that protrudes from the face of shaker housing 86. Inside shaker housing 86 is an electric motor connected to a mechanism that moves the vial grippers 88 to shake and thoroughly mix the contents of the vials.

Figure 9:
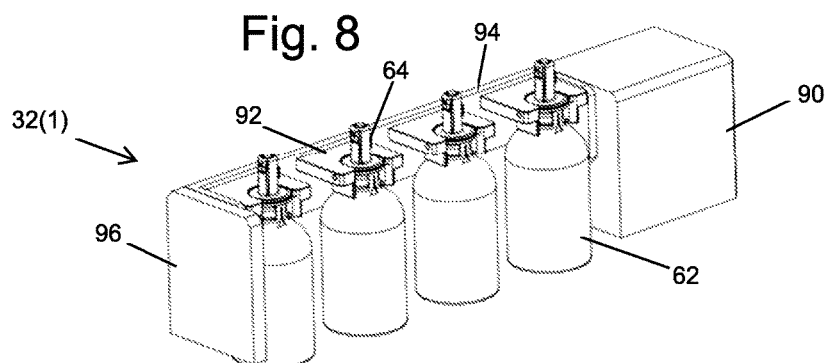
FIG. 9 schematically shows one of the vial flip modules.

FIG. 9 schematically shows one of the vial flip modules 32(1). The vial flip module comprises one or more (four are shown in this embodiment) flipper vial grippers 92 that grab the Equashield© vial adapters 64 attached to vials 62. All flipper vial grippers in the module are attached to a flipper bar 94. After the vial robotic arm assembly 28 has inserted each vial adapter 64 into a flipper vial gripper 92, a motor and gear box 90 that are contained in flipper base 96 are activated to rotate flipper bar 94; thereby flipping, i.e. inverting the vials.

FIG. 10 schematically shows an IV bag base 26. The operator inserts IV bags 100 into safety cabinet 10 laying the IV bag on bag rest 102 and, if needed, connecting IV bag 100 to bag hook 98. Then the operator inserts Equashield© spike adapters 104 into the two spike ports of the IV bag. The spike adapters are then fixed in place and locked in spike adapter mounts 106, from which they can be released by means of spike adapter release button 108 to allow removal of the IV bag from safety cabinet 10. In cases in which the prescription is delivered to the patient by injecting it from a syringe, an Equashield© plug 110 is fixed and locked in a dedicated mount 112 from which it can be released by plug lock release mechanism 114. The syringe pump robotic arm assembly will connect the filled syringe to the plug. In cases when there are other prescription containers like an elastomeric pump or other type of infusion pump cartridges an Equashield© male Luer Lock 116 is mounted and locked to mount 118. Male Luer Lock 116, which can be released by release button 120, serves as an adaptor between the cartridge's female Luer connection and an Equashield© syringe.

FIG. 11A schematically shows the syringe magazine 40 and FIG. 11B is an enlarged view of area "B" in FIG. 11A. The syringe magazine is a conveyor belt 152 driven by an electric motor located inside motor housing 148. A plurality of syringe mounts 150 are attached to conveyor belt 152. Prior to a preparation session the operator loads Equashield© syringes of different sizes—according to a list that appears on the operator screen 20. The cameras and processors of the system can identify which of the syringe mounts 150 are empty and activate the conveyor motor to move an empty syringe mount 150 in front of the insertion door 24 door allowing the operator to reach through the door and hang a syringe on the syringe mount. When the system senses that the mount is filled and that no object, e.g. hands, is inserted through the syringe door, it moves the belt to bring the next empty mount in front of the door.

Figure 12:
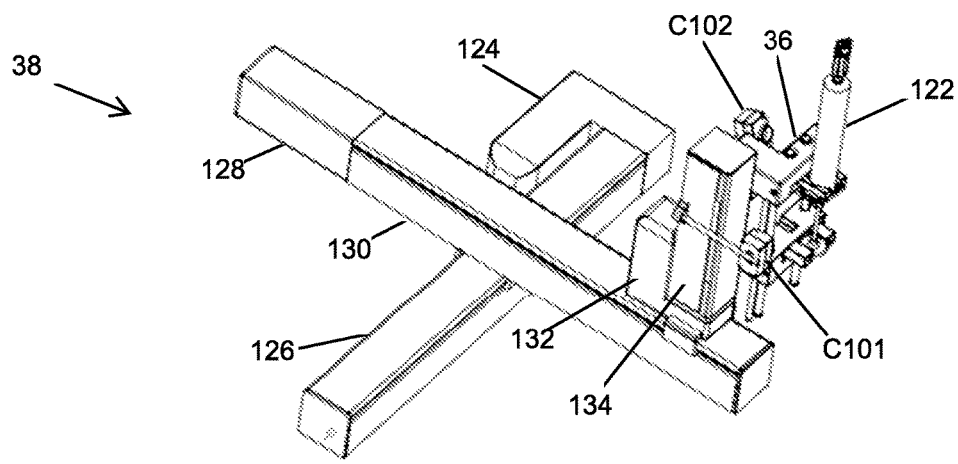
FIG. 12 schematically shows the syringe pump robotic arm assembly.

FIG. 12 schematically shows the syringe pump robotic arm assembly 38. Under direction of the software of the system syringe pump robotic arm assembly is configured to (1) move the syringe pump in order to remove an empty syringe from the syringe magazine; (2) to move the syringe to the proper location under working surface 16 (3) to connect the syringe to one of the vials (through the vial adaptor) in the vial flip mechanisms 32 (4) to withdraw liquid from the vial; (5) to disconnect the syringe; (6) to move the filled syringe and connect it to an IV bag via the Equashield© spike adaptor connected to it; (7) to wait until the syringe pump 36 is activated to inject the contents of the syringe into the IV bag; and (8) to repeat the process until the adequate dose has been injected to the IV bag and finally to move the empty syringe to and release it into a disposal bin. The syringe pump robotic arm assembly executes steps (1) to (8) mutatis mutandis in the cases when the prescription is delivered to the patient by infusion pump cartridge.

In the case the drug is delivered to the patient by injecting it from a syringe, the syringe pump robotic arm assembly executes steps (1) to (4) and then connects the syringe to the Equashield® Protective Plug 110 on the IV bag base 26 and leaves it there i.e. releases its grip. The operator, then, pulls the Protective Plug out from its mount 112, with the syringe attached to it through a slot in the work surface 16 and carries the syringe with attached plug out of the safety cabinet through the open front of the safety cabinet above surface 16.

Syringe pump robotic arm assembly 38 is configured to pick up syringes and to move them to different stations under the work surface 16. The degrees of motion required to carry out these tasks are provided by x-axis motor and gear box 124 that, for example, turn a screw to move y-axis motor and gear box 128 in the x-direction along x-axis beam 130. Y-axis motor and gear box 128 turns a screw to move z-axis motor and gear box 132 in the y-direction along y-axis beam 130. Z-axis motor and gear box 132 moves syringe pump 36 up and down in the z-direction along z-axis beam 134.

Shown in FIG. 12 are the approximate locations of two video cameras that are part of the control and verification module. Camera C101 is placed at a location where it can inspect the syringes that are attached to syringe pump robotic arm assembly 36. The images from this camera are analyzed by software algorithms adapted to determine the volume to which the syringe plunger was pulled and verify that it is the correct volume according to the prescription. In working with syringes one common problem is the presence of air bubbles together with the liquid that is drawn into the barrel of the syringe. Air bubbles affect the accuracy of the dosage and, if injected into a blood vessel of the patient, can cause serious and sometimes fatal complications. Because of the difference in the optical properties there is a visually notable difference between air and the liquid in the syringe. Camera C102 is placed at a location where it can inspect filled syringes that are attached to syringe pump 36. At the background of this camera, the syringe is lighted with a light source oriented at an angle smaller than the drug's optical critical angle. That means the light that reaches the bubble's surface stays trapped in the fluid within the syringe, and the bubble surface is darkened. In an embodiment of this application the light can be polarized. The images from this camera are analyzed by software algorithms adapted to identify this difference and thus the presence of bubbles in the images of the filled syringe.

Figure 13:
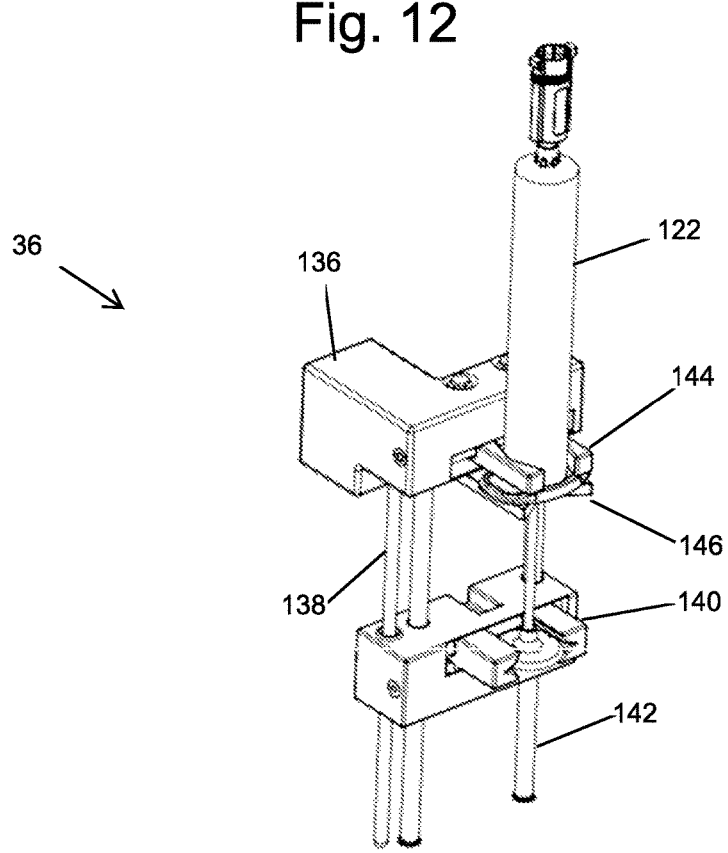
FIG. 13 schematically shows the syringe pump.

FIG. 13 schematically shows the syringe pump 36. An Equashield© syringe is firmly attached to the housing 136 by means of syringe barrel gripper 144 and syringe bottom gripper 146. The plunger cap is secured in syringe plunger gripper 140. Syringe plunger gripper 140 can be moved up and down on pump rails 142 by means of lead a screw 138 that is rotated by a motor and gearbox inside housing 136; thereby drawing liquid into or ejecting it from the barrel of the syringe.

Figure 14:
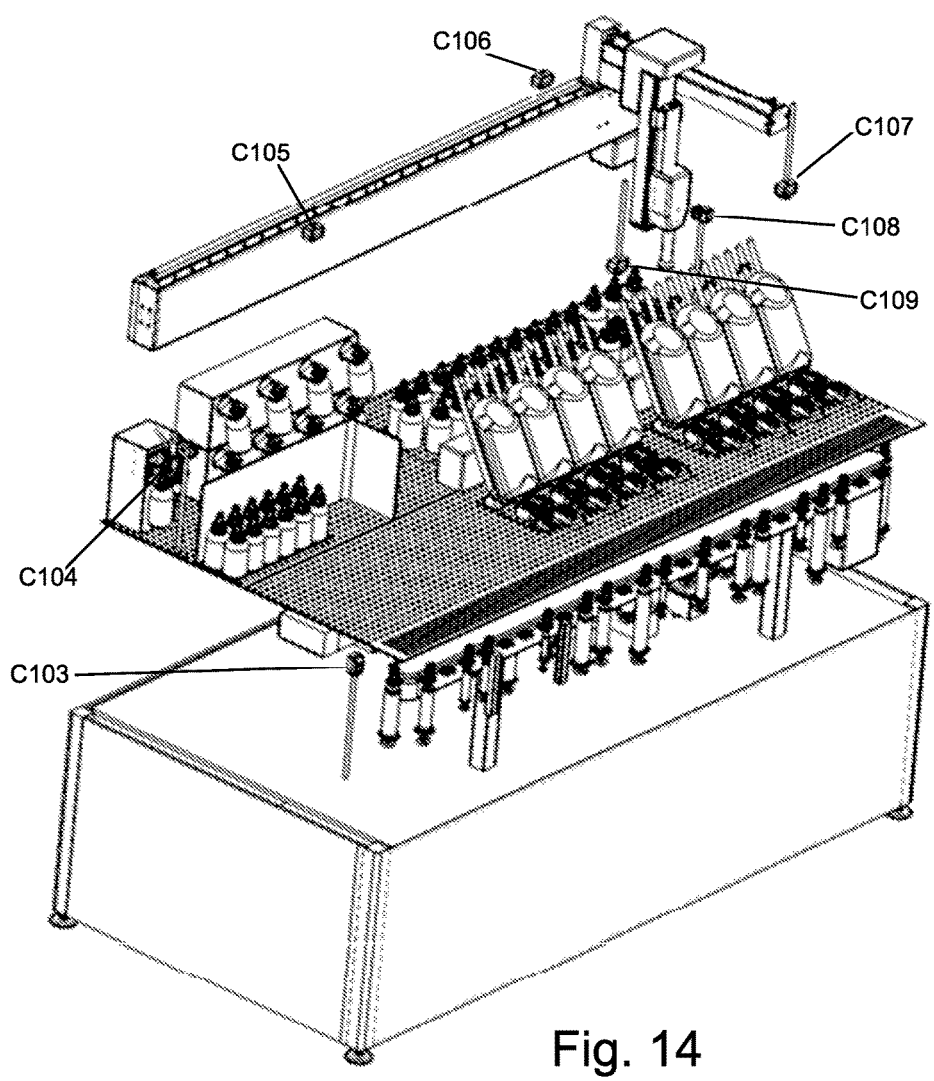
FIG. 14 schematically shows the approximate locations of some of the cameras in the safety cabinet of the invention.

FIG. 14 schematically shows the approximate locations of some of the cameras in the safety cabinet of the invention. The locations of these cameras are chosen to provide images that the algorithms in the processor of the control and verification module can interpret to provide the following information: camera C103 provides images used to identify the size of syringes loaded onto syringe magazine 40 and the position of their pistons; camera C104 provides images to be used by image processing algorithms to read the labels on the vials, which are therefore rotated in front of camera C104 as they are loaded into the vial insertion area 42; camera C105 provides images that enable the control system to determine the position of a specific vial in the vial insertion area 42; camera C106 provides images that enable the control system to determine the position of a specific vial in the vial internal storage area 34; camera C107 provides images used to identify the IV bags on the bases in module 26(2) and to read the prescription stickers attached to them; camera C108 provides images used to recognize a vial held by vial robotic arm assembly 28 before the vial is attached to a vial flip mechanism 32, and camera C109 provides images used to identify the IV bags on the bases in module 26(1) and to read the prescription stickers attached to them.

Embodiments of the safety cabinet can be provided with components to provide other capabilities. For example supplying ozone for sterilization of the entire interior of the safety cabinet or specific locations within the safety cabinet, for example sterilizing the septum in the vial connectors on the vial flipper before flipping the vials to connect syringes to the vials or the drug container connectors, i.e. spike adaptor, male Luer lock connector, and protective plug, before being connected to a syringe.

Embodiments of the system of the invention can include an IV bag emptying module or several modules. The IV bag emptying module is designed to remove air and/or excessive liquid from the IV bag in order to allow enough room in the bag to add drugs that have been prepared or to insure that the concentration of drug in the IV bag is the concentration that is specified for infusion to the patient. To operate the module the operator places the IV bag is put on a specially designed scale with the prescription sticker attached to it or place next to it. One of the bag's ports or any connector that is connected to its port, e.g. an IV bag spike adapter, is locked in place and connected to a fluid pump. The bag is supported with its ports facing upwards so that when the pump is activated first the air will be pulled out, and only then the liquid. The operator then pressed a start button. Following this an image of the bag and the prescription sticker is taken and the matching prescription is located in the system's database. According to the prescription and the data concerning the bag in the system's database, the system will calculate how mush fluid should be drawn out of the bag and the final weight the bag should reach accordingly. Then the pump draws the liquid from the bag, until the desired weight is reached. When the desired weight is reached the lock will open and the operator will be prompted to take the bag from the module.

Figure 15A:
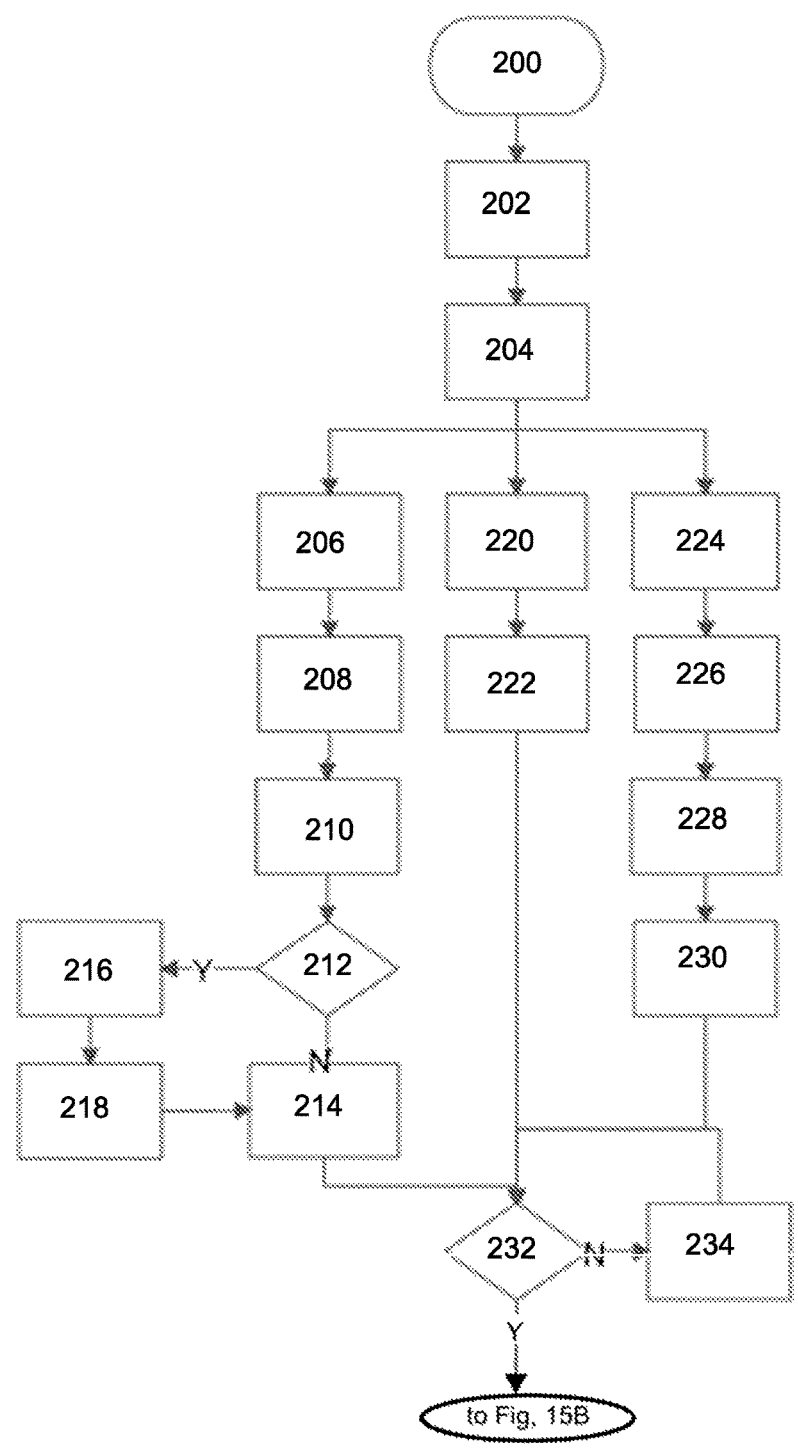
FIGS. 15A and 15B are two parts of a flow chart that describe in general the steps in the preparation of a drug prescription by the system of the invention.
Figure 15B:
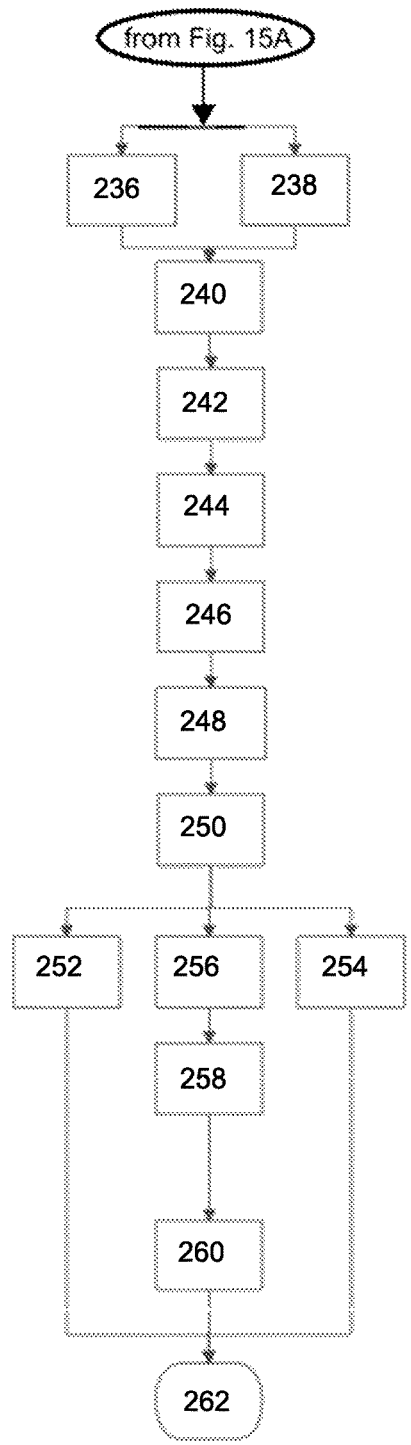

FIGS. 15A and 15B are two parts of a flow chart that describe in general the steps in the preparation of a drug prescription by the system of the invention.

The steps shown in FIGS. 15A and 15B are the following:

Step 200: A list of prescriptions is entered into the system by the supervisor or sent from another computer.

Step 202: The list is arranged according to prescription priority and sent to the operator's screen.

Step 204: The list appears on the operator's screen followed by a list of the components required to prepare the prescriptions, i.e. drugs (vials), syringes, and IV bags or other final containers.

Step 206: The operator feeds drug vials into the vial insertion area in the cabinet.

Step 208: The vials are picked up one at a time by the vial robotic arm assembly and are weighed by its load cell to verify that they contain the correct amount of drug. This step is necessary because sometimes previously used vials will be entered, meaning that their drug content is not what's written on their label. The weight of the empty vial is stored in the system database and subtracted from the weight measured by the load cell to determine the actual weight of the drug in the vial.

Step 210: The vial is rotated by the vial robotic arm as necessary to allow its label to be imaged by a camera while still held by the vial robotic arm assembly and image processing algorithms are used to read information on the labels and compare it with data stored in the system database to identify the vials and their contents.

Step 212: The system checks if the drug needs reconstitution.

Step 214: If the answer in step 212 is no, then the vial is moved by the vial robotic arm assembly to the vial internal storage area where they are stored in a known location determined by a software algorithm.

Step 216: If the answer in step 212 is yes, the vial is moved by the vial robotic arm assembly to the reconstitution module and filled with the appropriate type and volume of liquid.

Step 218: The vial is removed from the reconstitution module by the vial robotic arm assembly and moved to a shaker where it is shaken and then is moved by the vial robotic arm assembly to the vial internal storage area. (It is to be noted that in the embodiment of the safety cabinet described herein each of the two shaker modules can hold up to four vials, therefore steps 212, 216, and 218 can be carried out four times before each shaker module is activated and step 214 carried out for the reconstituted drugs.) In an embodiment of the invention the shaker starts rotating when the first vial is connected to it, and stops whenever a new vial needs to be connected or a vial has been sufficiently shaken.

Step 220: Syringes are fed by the operator into the syringe magazine in the cabinet.

Step 222: Each syringe put into the safety cabinet is imaged by a camera and stored in the syringe magazine. The syringes are put into the syringe magazine randomly. The system brings the nearest empty mount in front of the syringe insertion door and as soon as the syringe is put on the mount, it is imaged and the size of the syringe and its location in the syringe magazine is stored in the system's database.

Step 224: A label with the prescription details is printed and attached to the IV bags. In the case of a syringe or pump cartridge and sometimes also for IV bags the label is attached next to the container or on the IV bag base to avoid obscuring the labels on the containers.

Step 226: The IV bag or other final prescription container is placed and locked in an IV bag base in the cabinet.

Step 228: The prescription label on the container is read by the image processing algorithms.

Step 230: A matching prescription is located in the system's database.

Step 232: The system software algorithms check to see if an appropriate syringe and drug are available in the cabinet.

Step 234: If the answer to step 232 is no, then the system waits for the appropriate syringe and drug. (It is to be noted that steps 206 to 214, 220-222, and 224-230 are carried out sequentially and independently for each of the vials, syringes, and final containers loaded into the cabinet. Therefore it is possible that when step 230 is reached for the first final container that is loaded into the cabinet, steps 206 to 214 might not have been completed for the required drug and\or steps 220-222 might not have been completed for the required syringe—hence step 234.

Step 236: If the answer in step 232 is yes, then the vial robotic arm assembly seeks out and picks up the appropriate drug vial(s) from the vial internal storage area and puts the vial(s) in a vial flipper, which is then activated to flip the vial. (It is to be noted that in the embodiment of the safety cabinet of the invention described herein steps 230, 232, and 236 can be carried out up to four times for each of the two vial flipper modules before steps 238 to 262 are carried out for each of the vials in the flipper module.)

Step 238: Simultaneously with step 236 the syringe pump robotic arm assembly picks up the appropriate syringe from the syringe magazine and, after the vials have been flipped, connects the syringe to the appropriate vial. (It is to be noted that in the embodiment of the safety cabinet described herein there are two syringe pump robotic arm assemblies, which allows steps 238 to 262 to be carried out for two prescriptions simultaneously, with one syringe pump robotic arm assembly servicing the first vial flipper module and the other syringe pump robotic arm assembly servicing the second vial flipper module.)

Step 240: The syringe is connected to the vial in the flipper module.

Step 242: The syringe pump is activated to draw the correct volume of drug from the vial into the syringe.

Step 244: Cameras are activated and image processing algorithms determine that there are no bubbles in the liquid in the syringe and that the syringe plunger is pulled to the correct distance.

If a bubble is detected, the plunger is pushed to eject the bubble from the syringe and, if drug is still missing, the syringe is connected to a second vial. In case the wrong volume is detected, then, this is a major problem and the system automatically stops its operation and a big ERROR message appears on the operator's screen.

Step 246: If the answer in step 244 is yes, then the syringe pump robotic arm assembly disconnects the syringe from the vial and travels to the appropriate IV bag base (see step 226).

Step 248: The syringe pump robotic arm assembly connects the syringe to the final prescription container that is locked in the IV bag base and the syringe pump activated to push the contents of the syringe into the final prescription container.

Step 250: A camera is activated and image processing algorithms used to analyze the images to verify that the syringe is empty. If it is not then the pump is activated again until the correct volume of drug has been pushed into the final prescription container.

Step 252: The syringe pump robotic arm assembly carries used and emptied syringes to a waste deposit area and releases them into a waste bin.

Step 254: Simultaneously with step 252, the vial robotic arm assembly carries used and emptied vials to a waste deposit area and releases them into a waste bin. Vials from which only a portion of the contents have been withdrawn are returned by the vial robotic arm assembly from the vial flipper module to the vial internal storage area in the cabinet.

Step 256: Simultaneously with steps 252 and 254, an "OK" label is printed and attached to the prescription label on the final prescription container by the operator.

Step 258: A camera is activated and image processing algorithms analyze the images to identify the presence of the "OK" sticker.

Step 262: If the presence of the "OK" sticker is noted, then the final prescription container, i.e. IV bag, syringe, or IV pump cartridge, is unlocked from the IV bag base.

Step 264: The prescription preparation is completed and the operator removes the final prescription container from the safety cabinet and prepares it for transport from the pharmacy to the patient.

Figure 16A:
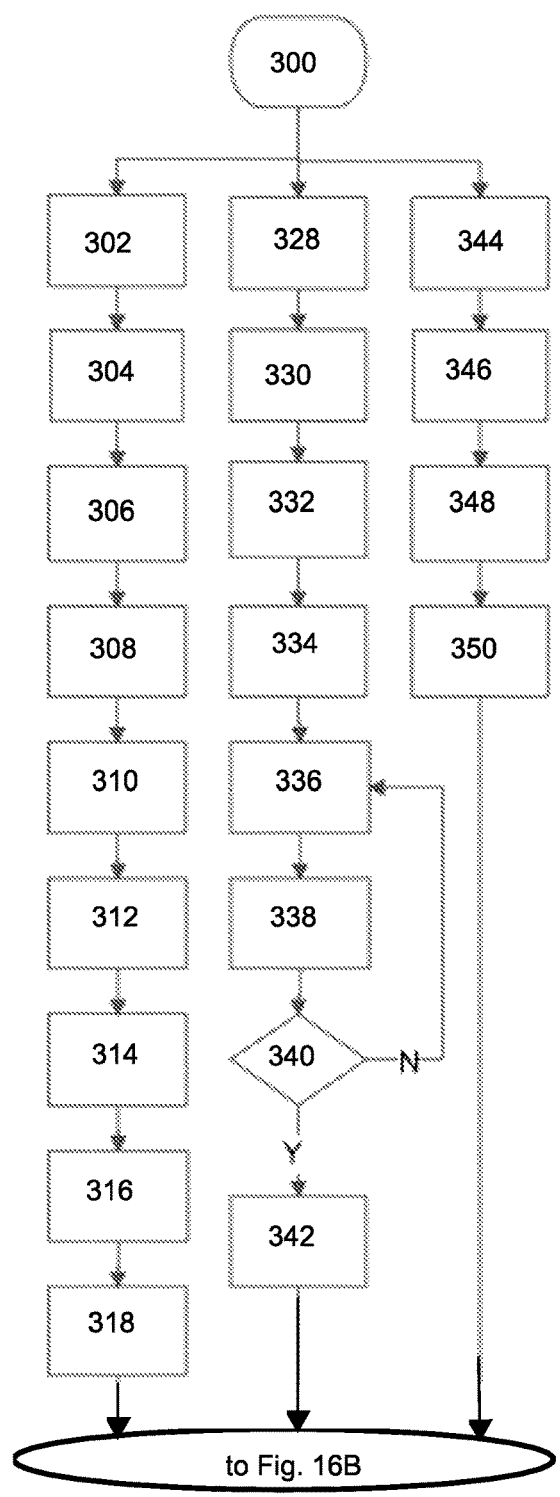
FIGS. 16A to 16C are three parts of a flow chart that describe the steps in the preparation of a specific exemplary drug prescription by the system of the invention.
Figure 16B:
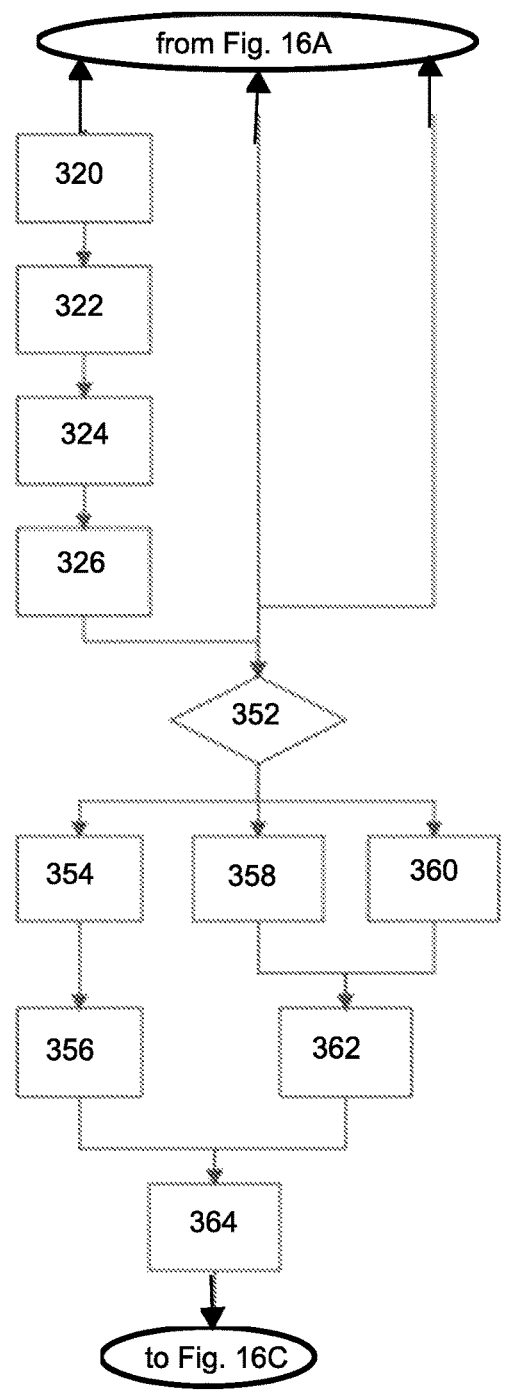
Figure 16C:
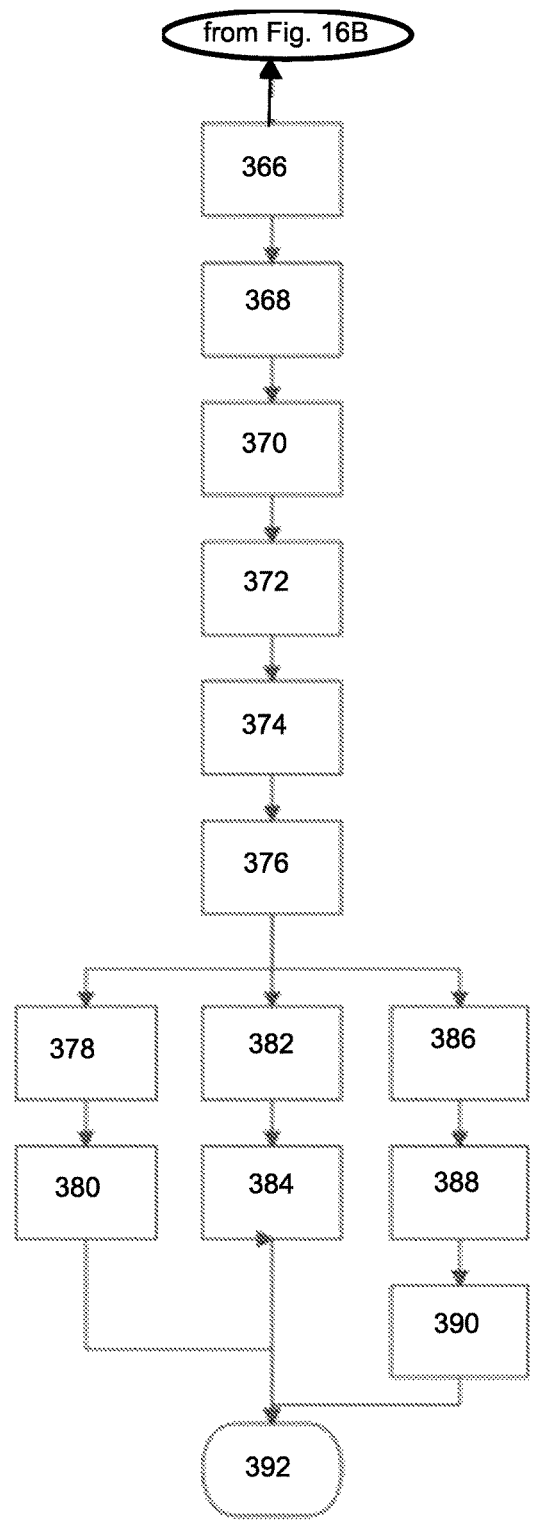

FIGS. 16A to 16C are three parts of a flow chart that describe the steps in the preparation of a specific exemplary drug prescription by the system of the invention.

Step 300: A prescription for 1200 mg of Cyclophosphamide (CP) diluted in 500 ml of NaCl in an IV bag is fed into the system.

Step 302: A request for 1200 mg CP appears on the operator's screen. The operator retrieves an appropriate drug vial from the pharmacy's store.

Step 304: The operator inserts a request to open the vial insertion door.

Step 306: The vial robotic arm assembly completes its current operation and returns to its homing position.

Step 308: The vial insertion door is unlocked and a signal confirming this appears on the operator's screen.

Step 310: The operator opens the door and inserts a vial containing the drug and closes the door.

Step 312: A vial position camera takes an image of the vial insertion area and image processing algorithms determine the location of the vial.

Step 314: The location of the vial is transmitted to the vial robotic arm assembly, which travels to that location and picks up and weighs the vial.

Step 316: The vial robotic arm assembly turns the vial in front of a camera to obtain images of the vial label.

Step 318: Image processing algorithms read the images of the label and identify the contents of the vial to be CP 100 ml-20 mg/ml lyophilized.

Step 320: The vial robotic arm assembly carries the vial to the reconstitution module and connects it to the NaCl (saline) port.

Step 322: The reconstitution connector is attached and to the vial and 100 cc of saline is injected into the vial.

Step 324: The vial robotic arm assembly removes the vial from the reconstitution module and carries the vial to the shaker and inserts it into a shaker vial gripper. The vial shaker then shakes the vial according to a predetermined shaking program and time.

Step 326: The robotic arm removes the vial from the shaker and takes it to the vial internal storage area of the cabinet.

Step 328: While steps 312-326 are being carried out, a request for a 60 ml syringe unit (1200 mg reconstituted CP=60 ml) appears on the operator's screen.

Step 330: The operator collects a 60 ml syringe unit from the pharmacy's store and inserts a request to open the syringe insertion door.

Step 332: The syringe conveyor brings an empty syringe mount in front of the door.

Step 334: A safety curtain is activated to make sure the conveyor doesn't move when the operator's hands are put through the syringe insertion door and the syringe insertion door is unlocked.

Step 336: The operator inserts the syringe into the mount and withdraws his hand.

Step 338: Another empty syringe mount is brought in front of the door in case the operator wants to put another syringe.

Step 340: The door is closed manually by the operator. When it is completely closed a sensor senses this and a locking mechanism, for example a magnetic lock, is activated.

Step 342: If the answer in step 340 is "no" i.e. the syringe insertion door is not closed, then the process returns to step 336. If the answer is "yes" then all new syringes on the conveyor are brought in front of a camera that takes images of each syringe that image processing algorithms analyze to determine the volume of the syringe and the position of its plunger.

Step 344: While steps 312-326 and 338-342 are being carried out a request to connect a 500 ml NaCl IV bag to a specific one of the IV bag bases, e.g. base 7 (this base is mentioned merely to illustrate the process).

Step 346: The operator takes the required IV bag from the pharmacy's store, attaches the prescription label on or near it, attaches the bag to the base, locks the Spike Adaptor in its mount, and presses a "start" button (switch) either on the base (not shown in the figures) or on the operator's screen.

Step 348: A camera takes an image of the prescription label and the label showing the contents of the IV bag.

Step 350: Imaging processing algorithms analyze the image from step 348 and match the prescription label to a prescription in the system's database.

Step 352: The algorithms in the systems processor compare the results from steps 318, 342, and 348 to confirm that the syringe, drug, and IV bag that are appropriate for the prescription in step 300 have been loaded into the safety cabinet.

Step 354: The vial robotic arm assembly is instructed by the processor to go to the location in the vial storage area where the vial was placed earlier, to pick up the correct vial, carry the vial to a vial flip mechanism module, and to connect the vial to one of the flipper vial grippers.

Step 356: The vial flip mechanism is activated to turn the vial upside down.

Step 358: The syringe conveyor is activated to move the appropriate syringe to a syringe pickup location.

Step 360: A syringe pump robotic arm assembly moves to the pickup location.

Step 362: The syringe pump robotic arm assembly removes the syringe from the syringe mount on the conveyor.

Step 364: The syringe pump robotic arm assembly connects the syringe to the vial adapter in the vial flipping mechanism.

Step 366: The syringe pump is activated to draw 60 ml CP from the vial.

Step 368: With the syringe still connected to the vial two images of the syringe are taken and analyzed by image processing algorithms to determine the volume of drug inside the syringe and to verify that there are no bubbles in the liquid in the syringe Step 370: Assuming that all is ok in step 268, the syringe pump robotic arm assembly disconnects the syringe from the vial, travels to the port in the spike adapter mount in the IV bag base and connects the syringe to the spike adapter.

Step 372: The syringe pump is activated to push the contents into the IV bag.

Step 374: The syringe pump is activated to draw 0.2-5 ml of fluid from the IV bag and to re-inject it to flush the port.

Step 376: An image of the syringe is taken and analyzed by image processing algorithms to verify that all contents of the syringe have been pushed into the IV bag.

Step 378: The vial flipper mechanism is activated to return the vial to an upright orientation.

Step 380: The vial robotic arm assembly attaches itself to the vial, removes the vial from the flipper mechanism, and moves the vial back to the internal vial storage area or to a waste bin if the vial is empty.

Step 382: The syringe pump robotic arm assembly moves the pump to above a waste bin.

Step 384: The syringe pump robotic arm assembly releases the syringe allowing it to fall into the waste bin.

Step 386: The system's printer prints a "FINISH" or "OK" label.

Step 388: The operator sticks the label on the IV bag.

Step 390: An image is taken of the IV bag and if the image processing algorithms determine that a "FINISH" label is on the bag, the bag is released from the IV bag base.

Step 392: The prescription preparation is completed and the operator removes the IV bag from the safety cabinet and prepares it for transport from the pharmacy to the patient.

Although embodiments of the invention have been described by way of illustration, it will be understood that the invention may be carried out with many variations, modifications, and adaptations, without exceeding the scope of the claims.

BIBLIOGRAPHY

1. NIOSH Alert, Preventing Occupational Exposure to Antineoplastic and Other Hazardous Drugs In Healthcare Setting (September 2004).
2. USP General Chapter <797>, 2011.
3. Dwight D. Kloth, Guide to Prevention of Chemotherapy Medication Errors, Clinical Oncology News Special Edition 2009, No. 2, Pages 107-114.
4. Jonathan R. Nebeker et al. High Rates of Adverse Drug Events in a Highly Computerized Hospital, ARCH INTRN MED/Vol 165, May 23, 2005, pages 1111-1116.
5. Kathleen E. Walsh et al. Medication Errors Among Adults and Children With Cancer in the Outpatient Setting, J. Clin Oncol 27:891-896, 2008.
6. http://www.livescience.com/15721-nurses-exposed-toxic-cancer-drugs.html
7. James Couch, Christine West, Chemotherapy Drug Exposure at an Oncology Clinic—Florida, NIOSH Health Hazard Evaluation Report, HETA 2009-0148-3158, June 2012.

The invention claimed is:

1. A system designed to assist a hospital pharmacy in compounding of medications comprising hazardous drugs, the system comprising:
   a. a biological safety cabinet comprising a high efficiency particulate air (HEPA) filter and fans;
   b. at least two robotic arm assemblies;
   c. a plurality of operational stations adapted to perform specific tasks related to a compounding process;
   d. a plurality of cameras each installed at a specific location in the safety cabinet or on the robotic arm assemblies, each camera dedicated to provide real time digital images of a stage of a preparation process carried out at that location;
   e. a system processor comprising: image processing algorithms to analyze the images received from the cameras; custom made algorithms to plan timing and motions of the robotic arm assemblies and other devices inside the safety cabinet; custom made algorithms to execute numerous comparisons and checks that are carried out to minimize errors in preparing the medications; and custom made software that manages the whole process and manages data flow and a system database; and
   f. communication channels between the system processor, the at least two robotic arm assemblies, the plurality of operational stations, and the plurality of cameras;
   wherein:
      i. at least one of the robotic arm assemblies comprises a vial gripper assembly and is adapted to move vials within the safety cabinet and at least one of the robotic arm assemblies comprises a syringe gripper assembly and syringe pump and is adapted to move syringes within the safety cabinet;
      ii. the robotic arm assemblies are adapted to allow steps in the compounding process to be carried out automatically under guidance of the software and algorithms in the system processor without intervention by an operator or a supervisor;
      iii. the cameras and imaging process algorithms are adapted to provide real-time feedback control of all stages of the compounding process;
      iv. each of the robotic arm assemblies that is adapted to move vials comprises three mechanical arrangements configured to independently move a vial in three dimensions along three mutually orthogonal beams and each of the robotic arm assemblies that is adapted to move syringes comprises three mechanical arrangements configured to independently move a syringe in three dimensions along three mutually orthogonal beams; and
      v. the robotic arm assemblies are adapted to simultaneously move vials and syringes within the safety cabinet.

2. The system of claim 1 wherein the safety cabinet comprises:
   a. a work area above a working surface, the work area divided by a partition into a forward section and a rear section; the work area comprising:
      i. at least one intravenous bag base module located in front of the partition;
      ii. at least one reconstitution module located behind the partition, each reconstitution module adapted to allow at least one vial to be connected to it and to inject a predetermined volume of liquid into the vial;
      iii. at least one vial shaker module located behind the partition, each vial shaker module adapted to allow one or more vials containing reconstituted drugs to be connected to it and shaken for a predetermined period of time and predetermined shaking method;
      iv. at least one vial flipper module located behind the partition, each vial flipper module adapted to allow at least one vial to be connected to it and to invert the vials;
      v. a vial insertion area located behind the partition;

vi. a vial internal storage area located behind the partition; and vii. one vial robotic arm assembly comprising a vial gripper adapted to allow the vial robotic arm assembly to pick up and to rotate a vial, the vial robotic arm assembly adapted to allow it move a vial to any location behind the partition above the work surface and to release the vial at a new location or to connect the vial to and disconnect the vial from the reconstitution module, vial shaker module, and vial flipper module;

b. a closed area below the working surface comprising;

i. a syringe magazine comprising a plurality of syringe mounts attached to a conveyor belt driven by a motor, the syringe mounts adapted to allow a syringe to be hung on them by an operator; and ii. at least one syringe pump robotic arm assembly each syringe pump robotic arm assembly comprising a syringe gripper assembly and a syringe pump, adapted to pick up a syringe from the syringe magazine and to attach the syringe to a syringe pump, which is adapted to draw liquid into and to eject liquid from a barrel of the syringe; each syringe pump robotic arm assembly adapted to move a syringe to locations inside the closed area and to connect the syringe to and disconnect the syringe from vials, intravenous bags, and infusion pump cartridges; and to discard used syringes;

c. an operator's display screen.

3. The system of claim 1 additionally comprising at least one of: a supervisor's station, a label printer, a backup memory device, and a programmable logic controller adapted to receive instructions from the system processor and to activate the robotic arm assemblies and other operational stations inside the safety cabinet.

4. The system of claim 2 wherein after a syringe pump has pulled a dose of drug from a vial, at least one image of the syringe is taken to check that there is no air bubble in the syringe barrel and to verify the position of the syringe piston in order to check that the correct volume of drug was pulled, wherein the checks are carried out automatically by image processing algorithms.

5. The system of claim 4 wherein, after it has been verified that the syringe pump has pulled the correct volume of drug and that there is no air bubble in the syringe barrel, the syringe pump robotic arm assembly moves the filled syringe to an intravenous bag base module and connects it to a final prescription container that is locked in the intravenous bag base and from which the drug is to be administered to the patient.

6. The system of claim 5 wherein, if the final prescription container is the syringe, it is connected to a syringe plug or other syringe holder and disconnected from the syringe robotic arm assembly.

7. The system of claim 5 wherein, if the final prescription container is an intravenous bag or an infusion pump cartridge the syringe pump is activated to push the contents of the syringe into the final prescription container and an image of the syringe is taken and analyzed to verify that the syringe is empty before disconnecting it from the final prescription container.

8. The system of claim 2 wherein a system operator manually loads vials into the vial insertion area in a random fashion.

9. The system of claim 8 wherein, after the vials have been randomly placed in the vial insertion area by the operator, a picture of the vial is taken and the position of each vial is determined by an image processing algorithm, to allow sending the vial robotic arm assembly to pick the vials.

10. The system of claim 8 wherein, after the vials have been randomly placed in the vial insertion area by the operator, each vial is picked up by the vial robotic arm assembly and weighed and imaged and identified by the information on its label by the image processing algorithms and moved to a specific location in the vial internal storage area by the vial robotic arm assembly.

11. The system of claim 9 wherein, when a vial that has been previously placed in the vial internal storage area is required to fill a prescription, the software in the system processor sends instructions comprising the specific location at which the vial was inserted into the vial internal storage area to the vial robotic arm assembly.

12. The system of claim 1 comprising one vial robotic arm assembly and at least two syringe pump robotic arm assemblies wherein the components of the system and the interactions between them are adapted to allow two prescriptions to be compounded in parallel.

13. The system of claim 1 comprising components adapted to supply ozone for sterilization of the entire interior of the safety cabinet or for sterilization of specific locations within the safety cabinet.

14. The system of claim 1 wherein the components of the system and the interactions between them are adapted to allow separately performing each of the following pairs of operations:

a. reconstituting the drug in a vial while simultaneously identifying other vials;

b. identifying syringes while simultaneously identifying vials;

c. reconstituting the drug in a vial while simultaneously identifying syringes;

d. identifying vials while simultaneously either drawing a drug from a vial into a syringe or injecting a drug from a vial into a final prescription container;

e. identifying syringes while simultaneously either drawing a drug from a vial into a syringe or injecting a drug from a vial into a final prescription container; and f. reconstituting the drug in a vial while simultaneously either drawing a drug from a vial into a syringe or injecting a drug from a vial into a final prescription container.

* * * * *